(12) United States Patent
Dishong et al.

(10) Patent No.: US 10,085,632 B1
(45) Date of Patent: Oct. 2, 2018

(54) MOBILE DRIVER LICENSE EXAMINATION WORKSTATIONS AND SYSTEMS AND METHODS INCLUDING SAME

(71) Applicant: North Carolina Department of Transportation, Raleigh, NC (US)

(72) Inventors: Randy Dishong, Wake Forest, NC (US); Timothy Mark McLawhorn, Washington, NC (US)

(73) Assignee: NORTH CAROLINA DEPARTMENT OF TRANSPORTATION, Raleigh, NC (US)

( * ) Notice: Subject to any disclaimer, the term of this patent is extended or adjusted under 35 U.S.C. 154(b) by 179 days.

(21) Appl. No.: 15/288,464

(22) Filed: Oct. 7, 2016

Related U.S. Application Data

(60) Provisional application No. 62/239,703, filed on Oct. 9, 2015.

(51) Int. Cl.
*A61B 3/02* (2006.01)
*G06Q 20/20* (2012.01)
*G06Q 30/00* (2012.01)
*G03B 29/00* (2006.01)
*A47B 83/04* (2006.01)
*A47B 81/00* (2006.01)
(Continued)

(52) U.S. Cl.
CPC ............... *A61B 3/02* (2013.01); *A47B 31/04* (2013.01); *A47B 81/00* (2013.01); *A47B 83/001* (2013.01); *A47B 83/045* (2013.01); *B60P 1/00* (2013.01); *B60P 3/07* (2013.01); *G03B 29/00* (2013.01); *G06Q 20/20* (2013.01); *G06Q 30/018* (2013.01); *A47B 2031/003* (2013.01); *A47B 2083/003* (2013.01); *A47B 2220/0091* (2013.01)

(58) Field of Classification Search
CPC combination set(s) only.
See application file for complete search history.

(56) References Cited

U.S. PATENT DOCUMENTS 3,107,020 A * 10/1963 Dempster ............. B60P 1/6454
414/491
4,181,347 A * 1/1980 Clark ................... A61B 6/4405
280/763.1

(Continued)

*Primary Examiner* — Lisa Lea Edmonds
(74) *Attorney, Agent, or Firm* — Myers Bigel, P.A.

(57) ABSTRACT

A mobile workstation system includes a transport vehicle, a mobile workstation, and a deployment system. The transport vehicle includes a cargo volume. The mobile workstation includes: a wheeled carrier; a cabinet supported by the carrier, the cabinet defining at least one enclosed compartment and having selectively openable closures to provide access to the at least one compartment; and a plurality of operational components disposed in the at least one compartment. The mobile workstation is positionable in each of: a storage configuration wherein the operational components are contained in the at least one compartment with the closures in a closed position; and an operational configuration wherein the closures are open to provide access to the operational components and the cabinet forms a desk including a work surface. The deployment system is mounted in the transport vehicle and includes a powered engagement mechanism operable to load and unload the mobile workstation into and from the cargo volume of the vehicle.

20 Claims, 15 Drawing Sheets

(51) Int. Cl.
*A47B 83/00* (2006.01)
*A47B 31/04* (2006.01)
*B60P 1/00* (2006.01)
*B60P 3/07* (2006.01)
*A47B 31/00* (2006.01)

(56) References Cited

U.S. PATENT DOCUMENTS

| | | | | |
|---|---|---|---|---|
| 4,920,458 A * | 4/1990 | Jones | | A47B 83/001 |
| | | | | 248/917 |
| 5,282,341 A * | 2/1994 | Baloga | | A47B 83/001 |
| | | | | 49/41 |
| 5,537,700 A | 7/1996 | Way et al. | | |
| 5,694,199 A * | 12/1997 | Rodriguez | | A61B 3/022 |
| | | | | 351/223 |
| 5,755,478 A * | 5/1998 | Kamiya | | A61G 3/001 |
| | | | | 296/19 |
| 5,775,758 A * | 7/1998 | Eberspacher | | B60P 3/14 |
| | | | | 296/19 |
| 6,082,799 A * | 7/2000 | Marek | | B60P 3/14 |
| | | | | 296/19 |
| 6,179,358 B1 * | 1/2001 | Hirayama | | B60P 3/14 |
| | | | | 296/24.38 |
| 6,625,252 B2 * | 9/2003 | Mirabella | | A61B 6/4405 |
| | | | | 378/102 |
| 6,908,133 B1 | 6/2005 | Morton et al. | | |
| 7,360,813 B2 * | 4/2008 | Ting | | A61G 3/001 |
| | | | | 296/24.38 |
| 7,398,571 B2 | 7/2008 | Souke et al. | | |
| 7,478,855 B2 | 1/2009 | Lambarth et al. | | |
| 7,520,551 B2 | 4/2009 | Lambarth et al. | | |
| 7,540,047 B2 | 6/2009 | Lambarth | | |
| 7,540,547 B2 | 6/2009 | Lambarth et al. | | |
| 7,725,968 B2 | 6/2010 | Lambarth | | |
| 7,992,881 B2 * | 8/2011 | Edelblut | | A47B 83/001 |
| | | | | 280/206 |
| 8,322,802 B2 * | 12/2012 | Boxenbaum | | A47B 51/00 |
| | | | | 312/194 |
| 9,220,348 B2 * | 12/2015 | Stieler | | A47C 7/68 |
| 2007/0102946 A1 * | 5/2007 | Blackwell | | A61G 3/001 |
| | | | | 296/24.38 |
| 2009/0143652 A1 * | 6/2009 | Warburton | | G06F 19/3418 |
| | | | | 600/301 |
| 2010/0201165 A1 * | 8/2010 | Dankovich | | A47B 83/001 |
| | | | | 297/135 |
| 2011/0115245 A1 * | 5/2011 | Engelbrecht | | A61G 1/02 |
| | | | | 296/19 |

* cited by examiner

MOBILE DRIVER LICENSE EXAMINATION WORKSTATIONS AND SYSTEMS AND METHODS INCLUDING SAME

RELATED APPLICATIONS

The present application claims the benefit of and priority from U.S. Provisional Patent Application No. 62/239,703, filed Oct. 9, 2015, the disclosure of which is incorporated herein by reference in its entirety.

FIELD OF THE INVENTION

The present invention relates to workstations for administering driver license examinations and, more particularly, to mobile workstations for administering driver license examinations.

BACKGROUND OF THE INVENTION

It is sometimes necessary or desirable to administer motor vehicle operator license examinations (also referred to herein as "driver license examinations") at locations outside of standard brick and mortar state department of motor vehicle (DMV) offices where such examinations are typically offered. For example, some rural communities do not have a DMV examination office nearby, and some people may for various reasons be unable to conveniently access a DMV examination office even if the DMV office not very remote. The DMV may also wish to offer and process non-driver license identification documents (e.g., ID cards) and voter registrations at locations other than DMV examination offices.

Some DMVs use mobile examination equipment to offer the foregoing services. In some cases, the DMV employs a recreational vehicle (RV) in which a DMV examiner office has been installed. Some DMVs use mobile examination equipment that is stored and transported in small cases (i.e., similar to suitcases).

SUMMARY OF THE INVENTION

According to embodiments of the invention, a mobile workstation system includes a transport vehicle, a mobile workstation, and a deployment system. The transport vehicle includes a cargo volume. The mobile workstation includes: a wheeled carrier; a cabinet supported by the carrier, the cabinet defining at least one enclosed compartment and having selectively openable closures to provide access to the at least one compartment; and a plurality of operational components disposed in the at least one compartment. The mobile workstation is positionable in each of: a storage configuration wherein the operational components are contained in the at least one compartment with the closures in a closed position; and an operational configuration wherein the closures are open to provide access to the operational components and the cabinet forms a desk including a work surface. The deployment system is mounted in the transport vehicle and includes a powered engagement mechanism operable to load and unload the mobile workstation into and from the cargo volume of the vehicle.

In some embodiments, the mobile workstation is a motor vehicle operator license examination mobile workstation. The operational components include apparatus usable by an examiner to administer motor vehicle operator license examinations.

In some embodiments, the workstation, when in the operational configuration, defines a customer zone and an examiner zone on opposed sides of the workstation and the work surface, the apparatus usable by an examiner to administer motor vehicle operator license examinations are accessible to the examiner sitting in the examiner zone, and some of the operational components are apparatus usable by a customer taking a motor vehicle operator license examination and are accessible to the customer sitting in the customer zone.

In some embodiments, the apparatus usable and accessible by a customer sitting in the customer zone include a vision testing unit.

In some embodiments, the apparatus usable and accessible by a customer sitting in the customer zone include an electronic payment terminal.

In some embodiments, the operational components include a camera positioned to photograph a customer sitting in the customer zone.

In some embodiments, the deployment system includes a guide track affixed to the transport vehicle in the cargo volume. The deployment system further includes a trolley mounted on the guide track to travel axially along the guide track. The powered engagement mechanism includes a cradle arm configured to engage the mobile workstation and a force actuator to drive the cradle arm.

According to some embodiments, the carrier includes a height adjustment mechanism.

According to some embodiments, the cabinet includes a plurality of subcabinets, and each of the subcabinets defines a respective compartment containing one or more of the operational components and has a selectively openable closure.

In some embodiments, each of the subcabinets and the operational component(s) contained therein form a module that is secured to the carrier and removable from the carrier independently of the other subcabinets.

According to some embodiments, the mobile workstation includes electronic components disposed in a compartment of the cabinet, and at least one cooling fan operative to generate a flow of ambient air through the compartment to cool the electronic components.

In some embodiments, the mobile workstation includes a power supply connection to provide electrical power to one or more of the operational components.

In some embodiments, at least one of the closures is provided with a lock.

According to method embodiments of the invention, a method for providing a workstation, providing a mobile workstation system including a transport vehicle, a mobile workstation, and a deployment system. The transport vehicle includes a cargo volume. The mobile workstation includes: a wheeled carrier; a cabinet supported by the carrier, the cabinet defining at least one enclosed compartment and having selectively openable closures to provide access to the at least one compartment; and a plurality of operational components disposed in the at least one compartment. The mobile workstation is positionable in each of: a storage configuration wherein the operational components are contained in the at least one compartment with the closures in a closed position; and an operational configuration wherein the closures are open to provide access to the operational components and the cabinet forms a desk including a work surface. The deployment system is mounted in the transport vehicle and includes a powered engagement mechanism operable to load and unload the mobile workstation into and from the cargo volume of the vehicle. The method further includes: using the transport vehicle, transporting the mobile workstation in the cargo volume with the mobile workstation in the storage configuration; thereafter unloading the mobile workstation from the vehicle using the deployment system; and thereafter converting the mobile workstation to the operational configuration.

In some embodiments, the deployment system includes a guide track affixed to the transport vehicle in the cargo volume, the deployment system further includes a trolley mounted on the guide track to travel axially along the guide track, the powered engagement mechanism includes a cradle arm configured to engage the mobile workstation and a force actuator to drive the cradle arm, and the method includes, with the mobile workstation mounted on the trolley and supported by the cradle arm, sliding the trolley on the guide track toward an opening of the transport vehicle until the mobile workstation extends outwardly beyond the opening.

According to some embodiments, the method includes, after the step of sliding the trolley on the guide track toward an opening of the transport vehicle until the mobile workstation extends outwardly beyond the opening: with the mobile workstation supported by the cradle arm, lowering a frame assembly of the wheeled carrier to support the mobile workstation on the ground; thereafter lowering the cradle arm; and thereafter rolling the mobile workstation away from the transport vehicle.

In some embodiments, the carrier includes a powered height adjustment mechanism.

According to embodiments of the invention, a mobile workstation a wheeled carrier, a cabinet and a plurality of operational components. The cabinet is supported by the carrier. The cabinet defines at least one enclosed compartment and has selectively openable closures to provide access to the at least one compartment. The plurality of operational components are disposed in the at least one compartment. The mobile workstation is positionable in each of: a storage configuration wherein the operational components are contained in the at least one compartment with the closures in a closed position; and an operational configuration wherein the closures are open to provide access to the operational components and the cabinet forms a desk including a work surface. The mobile workstation is a motor vehicle operator license examination mobile workstation. The operational components are apparatus usable by an examiner to administer motor vehicle operator license examinations.

According to some embodiments: the workstation, when in the operational configuration, defines a customer zone and an examiner zone on opposed sides of the works station and the work surface; the apparatus usable by an examiner to administer motor vehicle operator license examinations are accessible to the examiner sitting in the examiner zone; some of the operational components are apparatus usable by a customer taking a motor vehicle operator license examination and are accessible to the customer sitting in the customer zone; the apparatus usable and accessible by a customer sitting in the customer zone include a vision testing unit; the apparatus usable and accessible by a customer sitting in the customer zone include an electronic payment terminal; and the operational components include a camera positioned to photograph a customer sitting in the customer zone.

In some embodiments, the cabinet includes a plurality of subcabinets, each of the subcabinets defines a respective compartment containing one or more of the operational components and has a selectively openable closure, and each of the subcabinets and the operational component(s) contained therein form a module that is secured to the carrier and removable from the carrier independently of the other subcabinets.

Further features, advantages and details of the present invention will be appreciated by those of ordinary skill in the art from a reading of the figures and the detailed description of the preferred embodiments that follow, such description being merely illustrative of the present invention.

DETAILED DESCRIPTION OF EMBODIMENTS OF THE INVENTION

Figure 1:
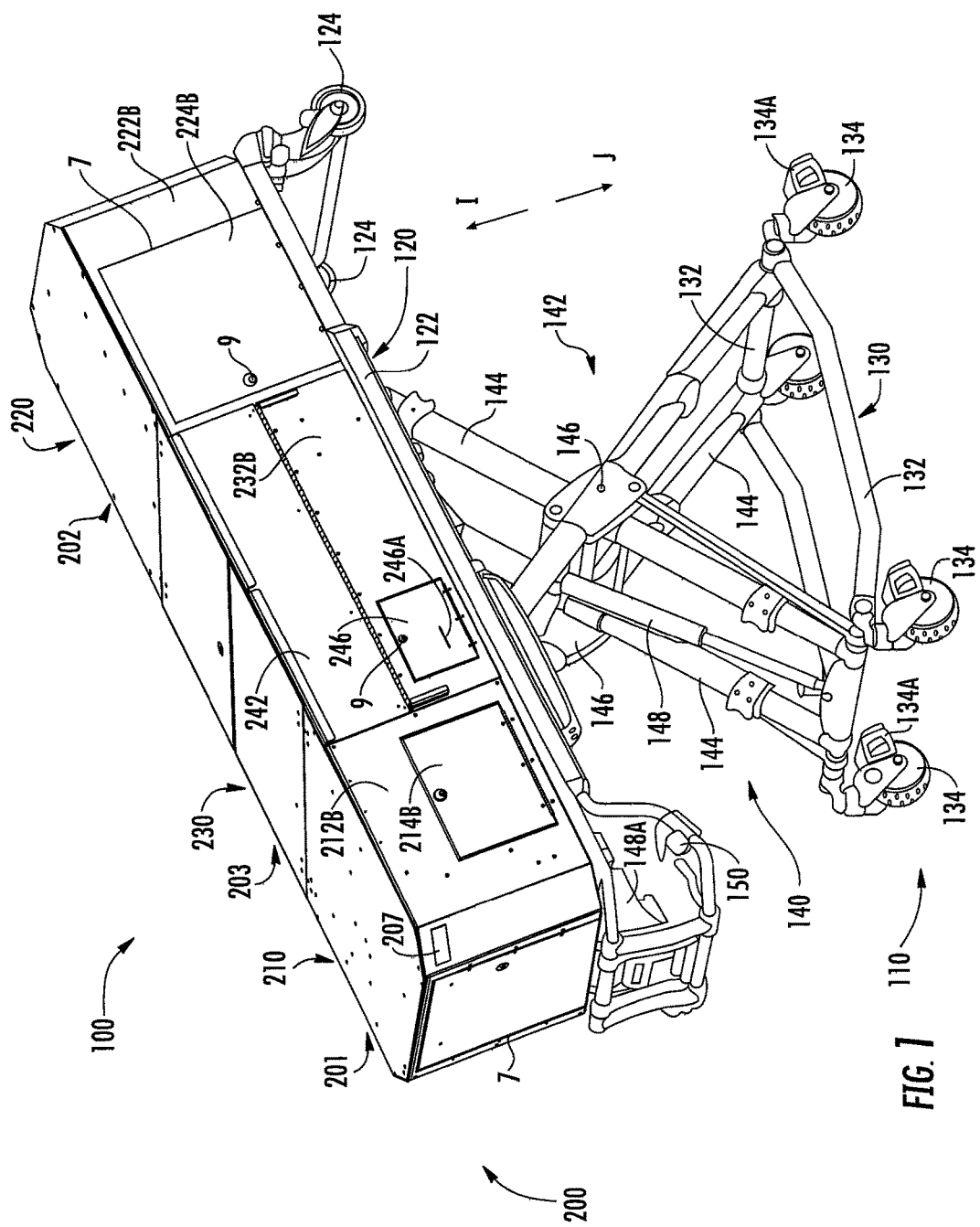
FIG. 1 is a rear perspective view of a mobile driver license examination workstation according to embodiments of the invention, the mobile driver license examination workstation forming a part of a mobile driver license examination workstation system according to embodiments of the invention.
Figure 2:
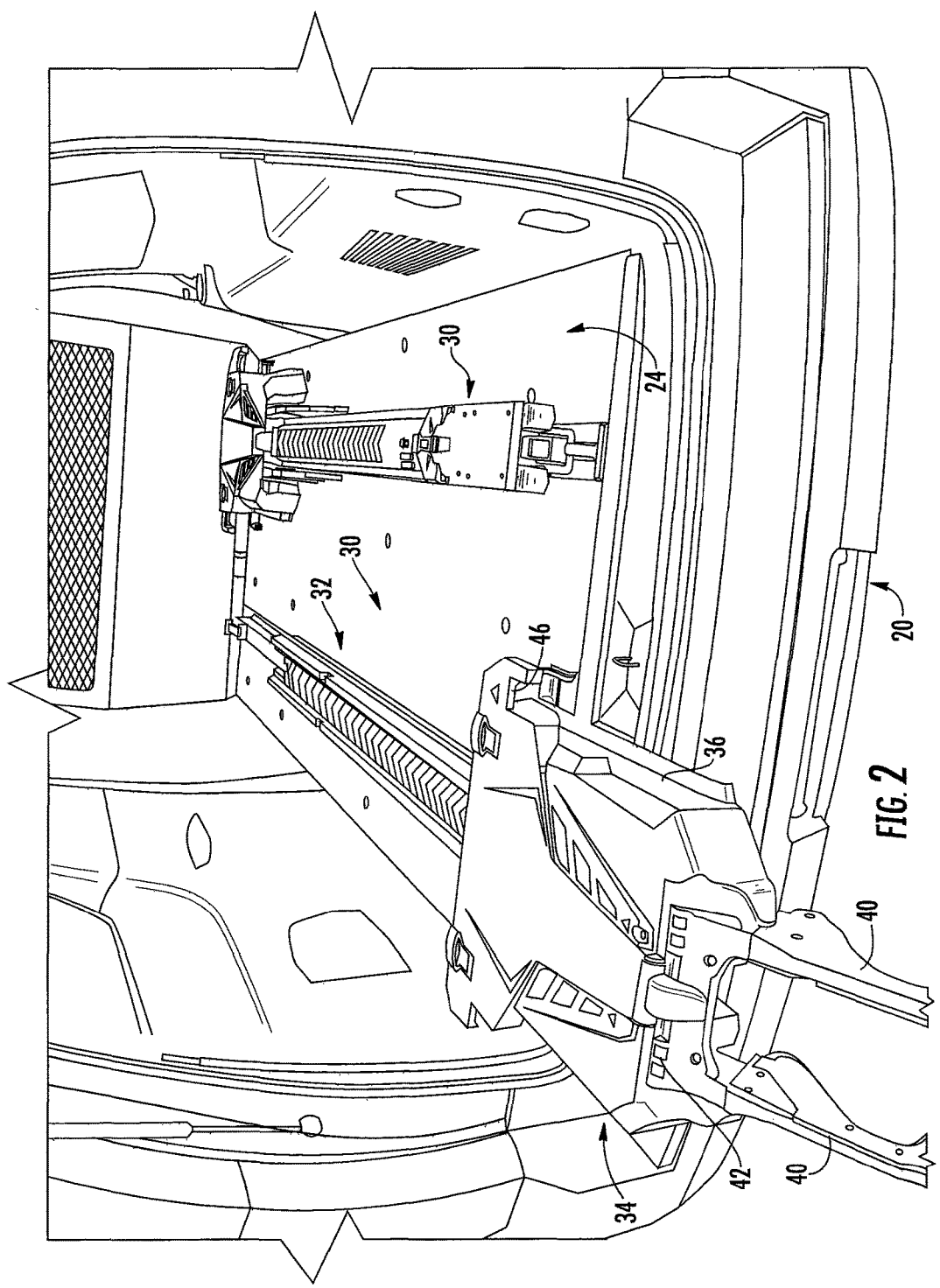
FIG. 2 is a fragmentary, front perspective view of a vehicle and a deployment system also forming a part of the mobile driver license examination workstation system.

The present invention now will be described more fully hereinafter with reference to the accompanying drawings, in which illustrative embodiments of the invention are shown.

In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90° or at other orientations) and the spatially relative descriptors used herein interpreted accordingly.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

As used herein, "motor vehicle operator license examination" refers to an examination administered by an examiner to determine whether a customer should be issued a motor vehicle operator license or other identification. A motor vehicle operator license may also be referred to herein as a "driver license" and a motor vehicle operator license examination may also be referred to herein as a "driver license examination".

With reference to FIGS. 1-15, a mobile driver license examination workstation system 10 according to embodiments of the invention is shown therein. The system 10 includes a transport vehicle 20, a deployment system 30, and a mobile driver license examination workstation 100. As described in more detail hereinbelow, the mobile workstation 100 is an integrated mobile motor vehicle operator examination workstation or office that can be used by an examiner to administer driver license examinations. In some embodiments, the system 10 and the workstation 100 are governed and controlled by a government agency, in some embodiments by a state governmental agency and, in particular, may be governed and controlled by a state department of motor vehicles (DMV). The mobile driver license examination workstation system 10 may also be referred to herein as a mobile workstation system 10 and the mobile driver license examination workstation 100 may also be referred to herein as a mobile workstation.

According to methods of the invention, the mobile workstation 100 can be loaded into the vehicle 20, transported to a desired work site (e.g., examination site) in the vehicle 20, deployed from vehicle 20 at the worksite using the deployment system 30, rolled to a desired location within the worksite, and used there to administer motor vehicle operator examinations or other operations. The mobile workstation 100 can thereafter be rolled to the vehicle 20, loaded into the vehicle 20 using the deployment system 3Q, and transported to a new location using the vehicle 20.

With reference to FIG. 2-6, the vehicle 20 may be any suitable motorized vehicle such as a truck, SUV or van. The vehicle 20 includes a chassis 22 including a cargo floor and defining a cargo volume 24 over the floor 22. The cargo volume 22 communicates with a rear portal or opening 28. The vehicle 20 includes a integral power supply 29 such as a battery that is charged by an alternator driven by an internal combustion engine.

With reference to FIG. 2-6, the deployment system 30 includes a guide track 32 and a trolley 34. The guide track 32 is affixed to the vehicle floor 22. The trolley 34 is mounted on the guide track 32 to enable the trolley 34 to slide on the guide track 32 along a track axis A-A in each of an outward direction B and an opposing inward direction C. The trolley 34 includes a body 36 slidably coupled to the track 32 and a pair of cradle arms 40 extending in the outward direction from the body 36. The cradle arms 40 are cantilevered from a cradle pivot 42 such that the cradle arms 40 can be rotated in each of an upward direction E and an opposing downward direction F. An actuator 44 (e.g., an electric motor) is configured to forcibly raise and lower the cradle arms in the directions E, F. As discussed below, the cradle arms 40 and the actuator 44 serve as a powered engagement mechanism for selectively engaging and disengaging the mobile workstation 100 and supporting and releasing the weight load of the mobile workstation. The deployment system 30 may further include a battery charger 48 and an integral battery 49. The deployment system 30 may further include one or more safety latches 46 or other safety mechanisms. The deployment system may be configured or modified as disclosed in U.S. Pat. No. 7,520,551, for example.

With reference to FIGS. 1 and 3-15, the mobile workstation 100 includes a carrier 110, a cabinet 200 and various functional components or peripherals as discussed in more detail below. The cabinet 200 and the functional components form a first (end) module 201, a second (end) module 202, and a third (center) module 203, which are each mounted on the carrier 210. The cabinet 200 and the functional components mounted therein collectively form a workstation subassembly 211 mounted on the carrier 110.

The carrier 110 includes a support frame 120, a base frame 130, and a height adjustment mechanism 140 connected between the support frame 120 and the base frame 130. The support frame 120 may include a plurality of connected rails 122 (e.g., metal tubing). The base frame 130 may similarly include a plurality of interconnected rails 132. The carrier 110 includes a pair of guide wheels 124 (e.g., as a part of the support frame 120, as shown). Wheels 134 are mounted on the base frame 130 and support the base frame 130 on the ground. The wheels 134 are provided with locking mechanisms 134A.

The height adjustment mechanism 140 and the base frame 130 form an adjustable frame assembly. The height adjustment mechanism 140 includes a linkage or scissor mechanism 142. The scissor mechanism 142 includes opposed sets of scissor legs 144 connected by pivot connections 146. A force actuator 148 (e.g., a linear actuator) is operatively connected to the linkage 142 and may be controlled by manipulation of an onboard switch or controller 150. The force actuator 148 can be actuated to drive the linkage 142 in a first direction I to increase the vertical distance between the support frame 120 and the base frame 130. The force actuator 148 can be actuated to drive the linkage 142 in a second direction J (opposite the first direction I) to reduce the vertical distance between the support frame 120 and the base frame 130. The force actuator 148 may be powered by an onboard battery 148A. Suitable carrier apparatus for the mobile workstation 100 include apparatus as disclosed in U.S. Pat. No. 7,725,968, the disclosure of which is incorporated herein by reference.

As discussed in more detail below, the cabinet 200 defines a plurality of compartments and a plurality of closures (doors and a drawer) that are selectively openable to provide access to the compartments. A plurality of functional or operational components (e.g., a vision testing unit, credit card reader, printer, network router, etc.) are disposed in compartments. The mobile workstation 100 is positionable in each of a storage configuration (FIGS. 1, 3-8 and 14) wherein the closures are closed to contain and protect the operational components, and an operational configuration (FIGS. 9-12) wherein the closures are open to provide access to the compartments and the components and the cabinet forms a desk including a work surface. In the operational configuration, the carrier may be adjusted to present the work surface at a height above the ground in a prescribed height range.

The cabinet 200 includes a base member or plate 208, a first subcabinet 210, a second subcabinet 220, and a third subcabinet 230. According to some embodiments, the subcabinets 210, 220, 230 are each secured to the base plate 208 by fasteners, for example, and the base plate 208 is in turn secured to the support frame 120 by fasteners, for example. In some embodiments, the subcabinets 210, 220, 230 are each removably secured to the base plate 208. In some embodiments, the subcabinets 210, 220, 230 are each secured to the base plate 208 by bolts 5. In some embodiments, the base plate 208 is secured to the support frame 120 by bolts 5. The subcabinets 210, 220, 230 may also be secured to adjacent ones of the subcabinets 210, 220, 230. The subcabinets 210, 220, 230 may each be removably secured to adjacent ones of the subcabinets 210, 220, 230 (e.g., by bolts).

In use and as will be better appreciated from the description below, the workstation 100 defines a customer zone ZC on one side thereof and an operator or examiner zone ZE on the opposite side thereof. The workstation 100 may further define a customer side zone ZS on one end.

The first subcabinet 210 includes a front panel 212A, a rear panel 212B, an inner side panel 212C, an outer side panel 212D, a top panel 212E and a bottom panel 212F collectively defining an enclosed chamber or compartment 210A. Ports 216 for cables and air flow are provided in the panel 212C. The bottom panel 212F is bolted to the base plate 208.

Doors 214A, 214B and 214D are provided on the panels 212A, 212B and 212D, respectively. The doors 214A, 214B and 214D each cover a respective portal 215A, 215B and 215C providing access to the compartment 210A. The doors 214A, 214B, 214D are each connected to their associated panel by a hinge 7 and a keyed lock latch mechanism 9. The door 214D is also provided with a privacy panel or shield 217 that is mounted on the door 214D such that it can be slid vertically upward into a shield position (FIGS. 10, 11 and 13) or vertically downward into a stored position within the boundary of the door 214D. A magnet 11 may be provided on the end wall or frame of the subcabinet 210 (FIG. 9) or on the door 214 to hold the door 214D in its open position.

The second subcabinet 220 includes a front panel 222A, a rear panel 222B, an inner side panel 222C, an outer side panel 222D, a top panel 222E and a bottom panel 222F collectively defining an enclosed chamber or compartment 220A. Ports 226 for cables and air flow are provided in the panel 222C. The bottom panel 222F is bolted to the base plate 208.

Doors 224A and 224B are provided on the panels 212A and 212B, respectively. The doors 224A and 224B each cover a respective portal 225A and 225B providing access to the compartment 220A. The doors 224A, 224B are each connected to their associated panel by a hinge 7 and a keyed lock latch mechanism 9.

The third subcabinet 230 includes a front panel 232A, a rear panel 232B, opposed side panels 232C, 232D, a top panel 232E and a bottom panel 232F collectively defining an enclosed lower chamber or compartment 230A. Opposed front and rear extension panels 242 are connected to the side panels 232C, 232D by hinges 7. Two cover panels 240 are connected to the top panels 212E, 222E by hinges 7 and supported by the extension panels 242. The cover panels 240, the extension panels 242, the top panel 232E and the side panels 212C, 222C of the subcabinets 210, 220 collectively define an enclosed upper compartment 230B. The cover panels 240 are secured in place by a keyed lock latch mechanism 9. Ports 236 for cables and air flow are provided in the side panels 232C, 232D. The bottom panel 232F is bolted to the base plate 208.

A top hatch or door 234 is provided in the top panel 232E. The top door 234 covers a portal 235 providing access to the lower compartment 230A. The door 234 is connected to the top panel 232E by a hinge 7 and opposed keyed lock latch mechanisms 9.

A drawer 246 is provided in the rear panel 232B and is secured by a keyed lock latch mechanism 9 The drawer 246 further includes a narrow slot 246A and a removable tray 246B defining a subchamber communicating with the slot 246A.

The subcabinets 210, 220, 230 may be formed of any suitable rigid material. According to some embodiments, the subcabinets 210, 220, 230 are formed of metal such as steel or aluminum. According to some embodiments, the subcabinets 210, 220, 230 are formed of powder coated steel. In some embodiments, the subcabinets are formed of metal sheeting having a thickness in the range of from about 1/16 to 1/8 inch.

Integral handles (e.g., hand hold slots, recesses, features or grips) 207 may be formed on or in each of the subcabinets 210, 220, 230.

The first module 201 includes the first subcabinet 210, a scanner 252, a touchscreen display 254, and a vision testing unit 256 disposed in the compartment 210A.

The scanner 252 (e.g., a flatbed scanner) is mounted on a tray with drawer slides 252A such that the scanner 252 can be pulled out of the subcabinet 210 through the portal 215A when the door 214A is open. The scanner 252 may be any suitable scanner such as the Xerox Documate 3220 flat bed scanner available from Xerox Corporation.

The touchscreen display 254 is mounted on a repositionable swingarm 254A such that the touchscreen display 254 can be pulled out of the subcabinet 210 through the portal 215B when the door 214B is open and repositioned for preferred access by a customer.

The vision testing unit 256 is mounted on a tray with drawer slides 256A such that the vision testing unit 256 can be pulled out of the subcabinet 210 through the portal 215C when the door 214C is open. The vision testing unit 256 is also mounted on a height adjustable (e.g., spring-loaded) riser 256O so that it can be stored in the compartment 210A in a low profile position and raised to a more comfortable height for the customer when extended. The vision testing unit 256 may also be mounted on a lazy Susan or turntable so that it can be rotated. The vision testing unit controller 256A is tethered to the vision testing unit 256 by a communications cable and may be disposed in the compartment 230B of the center subcabinet 230. The vision testing unit 256 may be any suitable vision tester such as the VS-V Standard Vision Screener Model No. 1155 available from Mast Concepts.

The second module 202 includes the second subcabinet 220 and a display monitor 260, a printer 262, antennae 264, and a power cord 266 disposed in the compartment 220A.

The display monitor 260 is mounted on a repositionable swingarm 260A such that the display monitor 260 can be pulled out of the subcabinet 220 through the portal 225A when the door 224A is open and repositioned for preferred access by a customer. The display monitor 260 may be an LCD or LED flatscreen monitor, for example.

The printer 262 is mounted on drawer slides 262A such that the printer 262 can be pulled out of the subcabinet 220 through the portal 225B when the door 224B is open. The printer 262 may be any suitable printer such as the E360dn MonoPrinter available from Lexmark International, Inc.

One or more components such as power blocks 285 may be mounted in the space or chamber 262B defined below the printer 262 in the compartment 220A. A rack 287 may be placed over the power blocks 285 and affixed (e.g., bolted) to the subcabinet 220 to conceal the power blocks and prevent tampering. The rack 287 may be provided with vent holes 287A and a slot 287B for wire routing.

The power cord 266 is mounted on a cable reel 266A in the compartment 220A. The power cord 266 extends out of the subcabinet 220 through an opening in the bottom panel 222F, for example. A length of the power cord 266 can be payed out from the reel 266A and rewound onto the reel 266A. In some embodiments, the power cord 266 is terminated with a standard connector 266B such as a three-prong plug. A surge protector may also be mounted in the compartment 220A.

The antennae 264 are mounted on one of a cover panel 240 and the panel door 224B. The antennae 264 may include a Wi-Fi radio antenna and/or a cellular communications (e.g., 4G) antenna.

The third module 203 includes the third subcabinet 230 and a laptop computer dock 270, a camera 272, an electronic payment terminal (referred to herein as a credit card reader unit) 274, a signature acquisition pad unit 276, and a barcode reader 278 disposed in the upper chamber 230B. The third module 203 further includes a backup power supply 280, a power distribution module 282, an air intake fan 284A, an air exhaust fan 284B, electrical power and communications cables (not shown), a hardware network security module 289 and a communications network hub 290 disposed in the lower compartment 230A. A surge protector may also be disposed in the compartment 230A. The electrical power and communications cables (not shown) operatively connect various of the electronic components in each of the modules 210, 220, 230 to one another and power supplies.

The top panel 232E and the door 234 (when closed) form a deck or prescribed open work surface 231. The top panel 232E, the door panel 234, and the extension panels 242 (when deployed) form an extended work surface 233.

The laptop computer dock 270 is securely mounted to a platform 270A, which is in turn slidably mounted on the door panel 234. In other embodiments, the dock 270 may be fixedly mounted on the door panel 234. The laptop computer dock 270 may be any suitable computer docking device. In some embodiments, the dock 270 is configured to mechanically secure a laptop computer 270B and to provide communications connections from the laptop computer 270B to other electronic components of the workstation 100 (e.g., the router 290). The dock 270 may also provide an electrical power connection to a power supply of the mobile workstation 100 such as the power distribution module 270 and/or the backup power supply 280. The laptop computer 270B may be stored and transported in the cabinet 200 (e.g., on the dock 270 or in the lower compartment 230A), or may be separately transported. A USB hub may be provided on the door panel 234 or in another easily accessible location.

The camera 272 is mounted on a camera stand 272A that can be broken or folded down for storage and erected for operation. The stand 272A may include adjustment mechanisms to enable an operator to properly rotate or tilt the camera for photographs of the customer. The camera 272 may be any suitable camera 272 such as the Canon Mobile Solution camera tower with digital camera available from MorphoTrust USA, for example.

The credit card reader unit 274 is secured to the top panel 232E by a credit card reader base 274A. The base 274A may be a swivel base. The credit card reader unit 274 may be stored and transported in the cabinet 200 (e.g., on the base 274A or in the lower compartment 230A), or may be separately transported. The credit card reader unit 274 may be any suitable electronic payment terminal (which may be referred to as a point of sale terminal, credit card terminal, EFTPOS terminal, or PDQ terminal) configured to interface with electronic payment cards to make electronic funds transfers. Suitable credit card reading and processing devices may include the MX850 point of sale terminal available from VeriFone Systems, Inc., for example.

The signature acquisition pad unit 276 may be any suitable electronic signature acquisition and processing device such as the T-L460 SigLite 1×5 LCD Signature capture pad available from Topaz Systems, Inc., for example. The signature acquisition pad unit 276 may be secured to the work surface 231 or remain loose and tethered by its cabling.

The barcode reader 278 may be any suitable device such as the Xenon 1900 Area-Imaging handheld scanner available from Honeywell International, Inc.

The backup power supply 280 may be a battery. The backup power supply 280 may further include a battery charger to charge the battery from a power source external to the workstation 100 (e.g., via the power cord 266).

The power distribution module 282 may include a power block or blocks including electrical connectors (e.g., standard three-prong electrical sockets) and connected to a power source external to the workstation 100 (e.g., via the power cord 266).

The air intake fan 284A is mounted over an intake port 236A in the bottom panel 232F. The air exhaust fan 284B is mounted over an exhaust port 236B in the bottom panel 232F. In use, the fan 284A draws air into the compartment 230A through the port 236A and the fan 284B forces air out through the port 236B to generate a cooling flow of ambient air through the compartment 230A. Cooling air may also enter the compartment 230A through the side ports 236.

The hardware network security module 289 may be any suitable hardware-based network security device(s). The module 289 may include a hardware-based internet firewall and other IT intrusion protection security features such as encryption/decryption software or firmware. Suitable hardware network security modules may include the TippingPoint™ S10 Intrusion Prevention System available from Hewlett-Packard, Inc.

The communications network hub 290 may be configured to interconnect various of the electronic components to one another and as well as to external or remote terminals or networks. The network hub 290 may include a single integrated module or two or more separately packaged electronic components. The network hub 290 may include a WAN and/or LAN router or switch (e.g., an Ethernet router), a modem (e.g., a broadband modem and/or other signal processing circuitry), and one or more radios (e.g., a WiFi radio and/or a cellular communications radio). The radio(s) may transmit through the antennae 264. In some embodiments, the hub 290 is compliant with the Payment Card Industry Data Security Standard (PCI DSS).

The mobile workstation system 10 may be used as follows in accordance with some methods of the invention. It will be appreciated that the procedures, operations and advantages discussed below are not exhaustive of the uses and advantages of the system 10 or the workstation 100.

Figure 3:
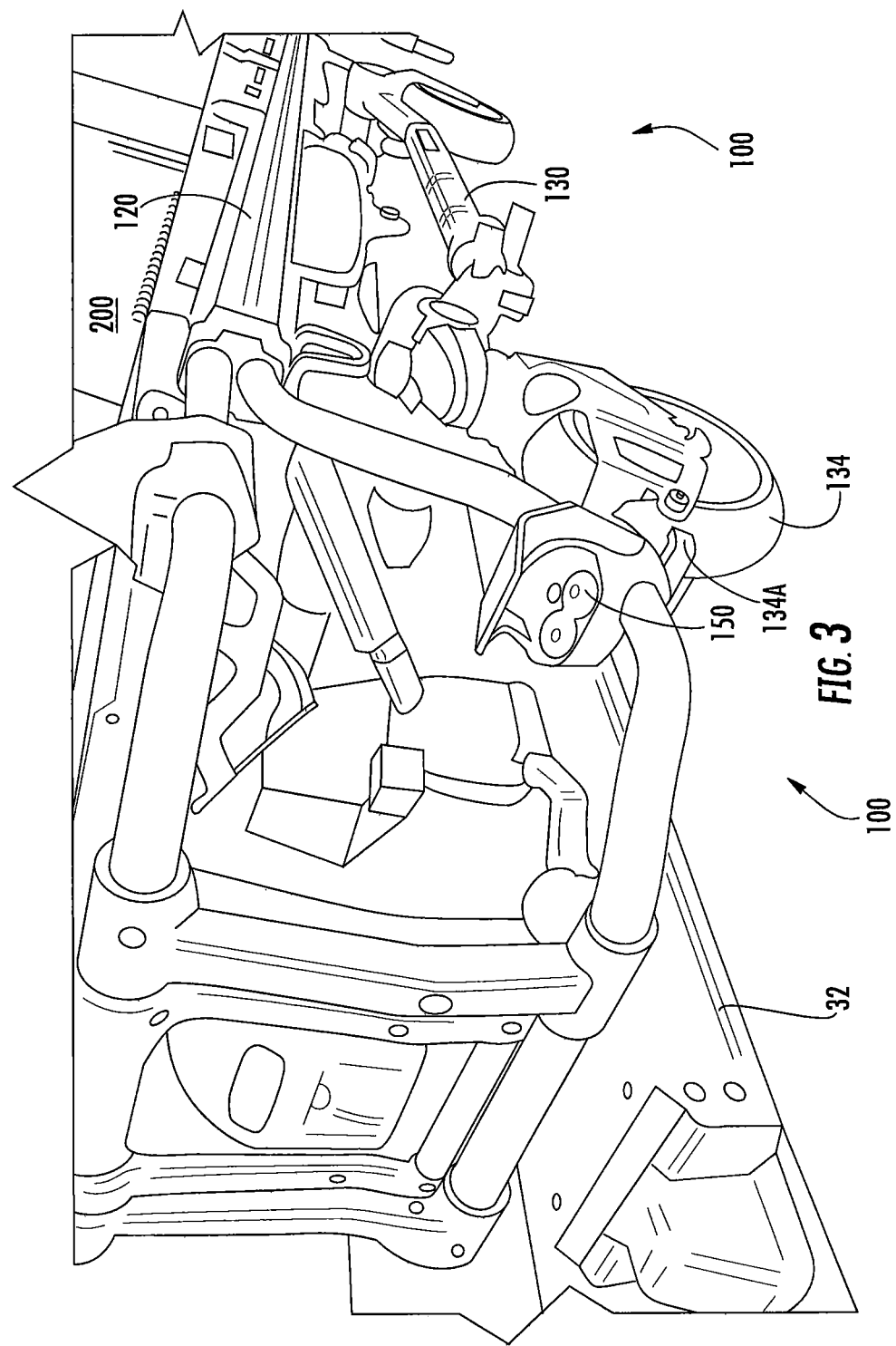
FIG. 3 is an enlarged, fragmentary, front perspective view of the mobile driver license examination workstation system.
Figure 4:
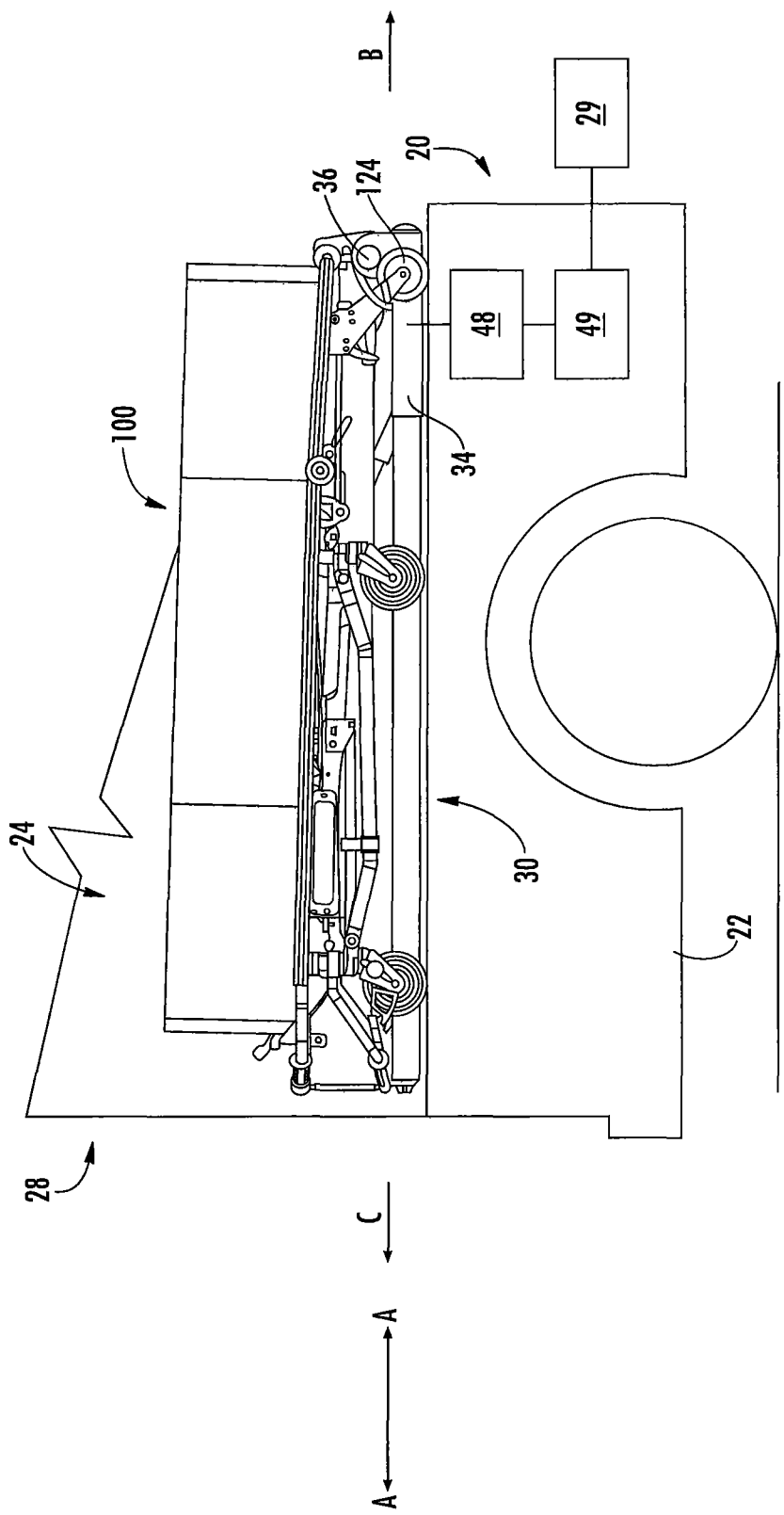
FIGS. 4-6 illustrate a sequence of steps for unloading the mobile driver license examination workstation from the vehicle using the deployment system.

For the purpose of discussion, the mobile workstation 100 is initially mounted on the deployment system 30 in the cargo volume 24 of the vehicle 20 in a transport position as shown in FIGS. 3 and 4. The cabinet 200 is configured in a closed configuration, wherein the aforedescribed components are contained in their respective compartments 210A, 220A, 230A, 230B and the doors 214A, 214B, 214C, 224A, 224B, 234, 240 and drawer 246 are locked closed by their latches 9, with the extension panels 242 raised.

The trolley 34 is located at the proximal end of the guide track 32 (i.e., proximate the end of the cargo volume 24 opposite the rear opening 28). The trolley 34 is locked in its axial position along the guide track 32. The guide wheels 124 of the carrier 110 are captured or latched in the safety latch mechanism 46 of the trolley 34 and the wheels 134 are supported by the floor 26 of the vehicle 20. The electrical connector of the carrier 110 may engage an electrical connector of the trolley 34 in order charge the battery 148A of the carrier 110 from the vehicle power supply 30. The backup battery 280 of the workstation 100 may also be charged via this or another connection to the vehicle power supply 30. Thus loaded, the vehicle 20 is driven to a desired worksite.

At the worksite, the vehicle door is opened to open the rear opening 28. Using the controller 150, the operator actuates the actuator 44 to raise the cradle arms 40 while the guide wheels 124 remain locked in the safety latch mechanism 46. The cradle arms 40 engage the underside of the support frame 120 and lift the carrier 110 off of the floor 26. A further actuator then releases the axial position lock between the trolley 34 and the guide track 32, permitting the trolley 34 to slide or translate along the guide track 32.

Figure 5:
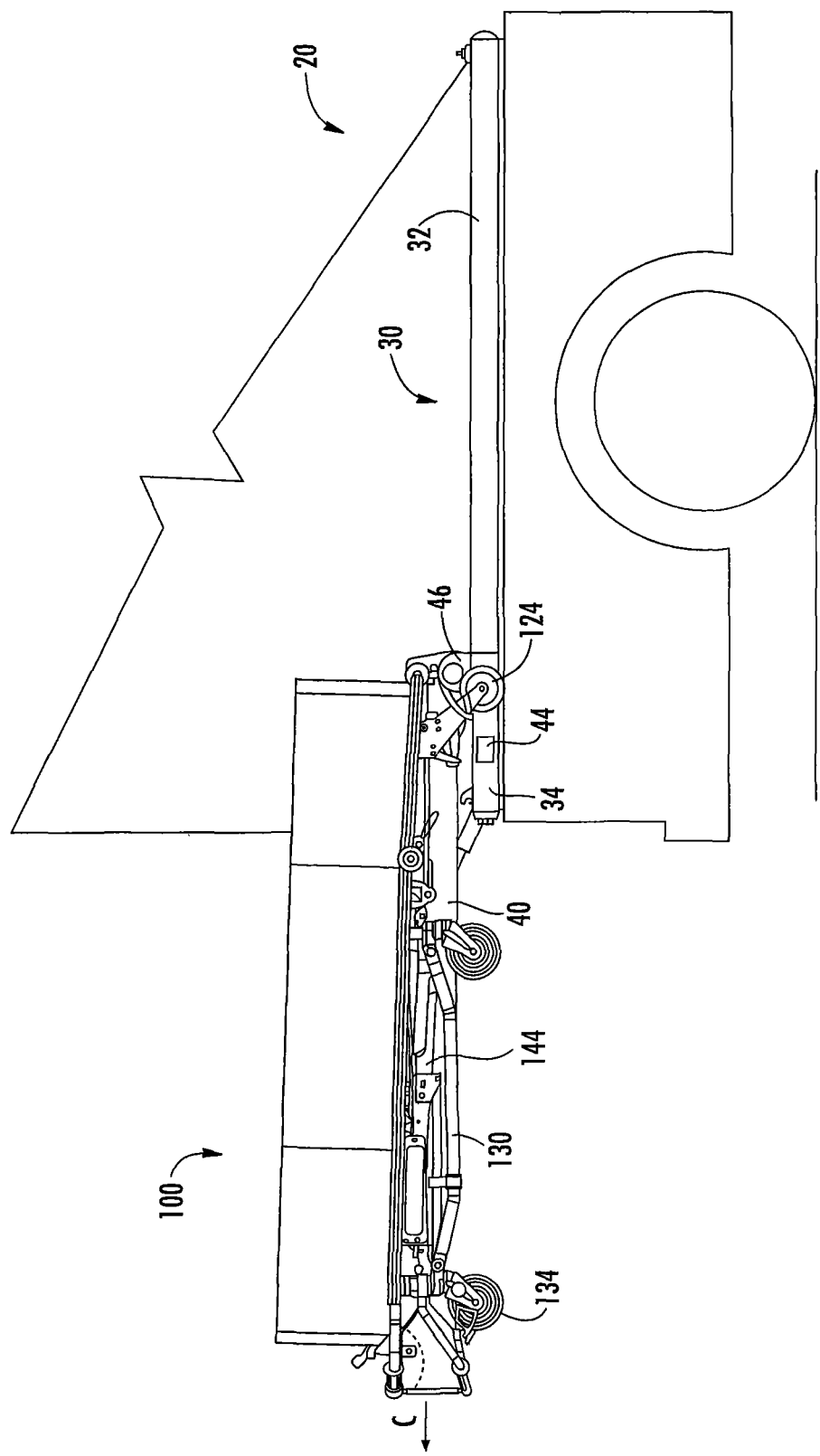

The operator then pulls the mobile workstation 100 in the direction B out through the opening 28 into the extended position of FIG. 5. In the extended position, the workstation 100 is supported by and cantilevered from the cradle arms 40. The guide wheels 124 remain locked in the safety latch mechanism 46.

Figure 6:
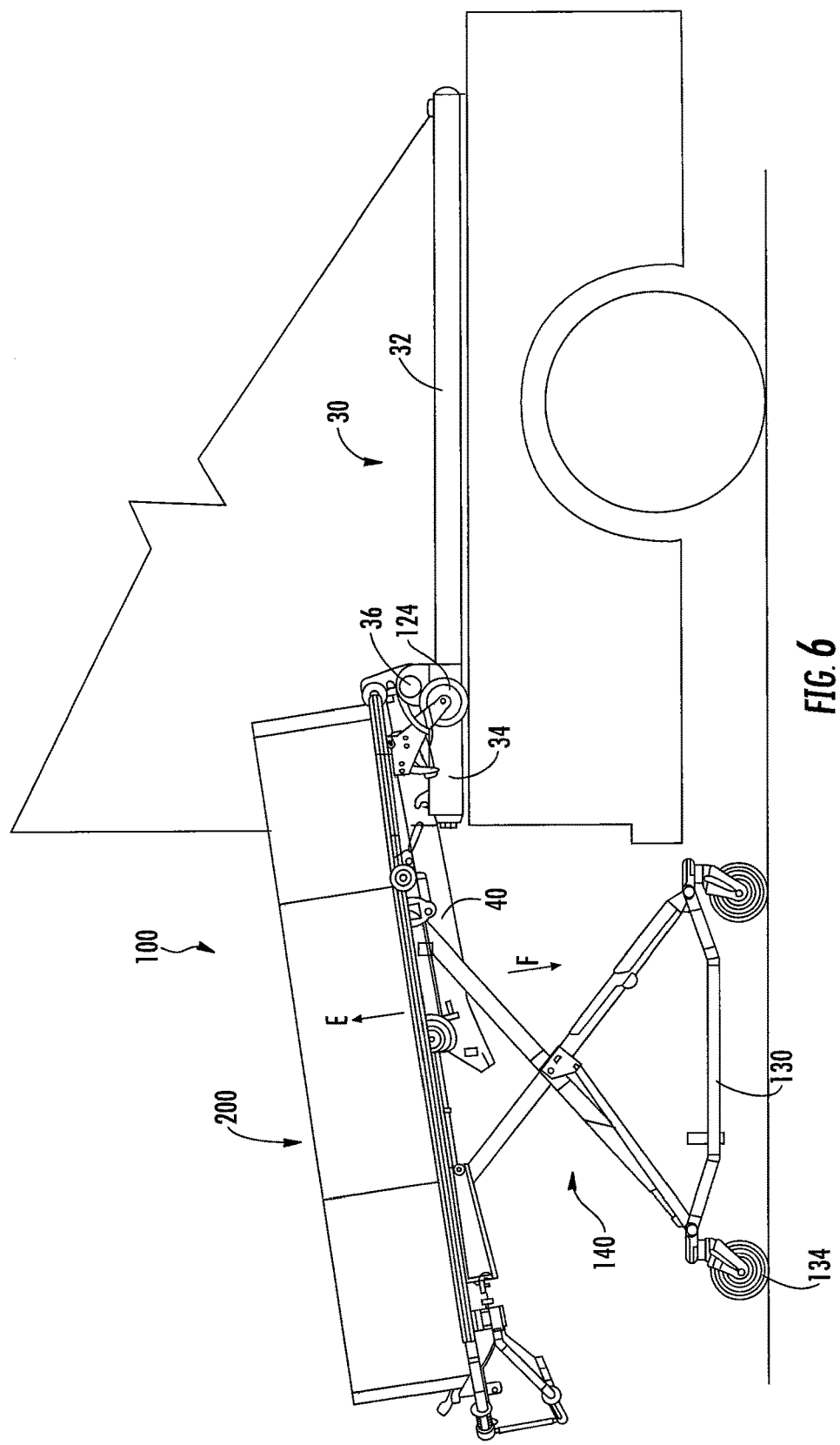
Figure 7:
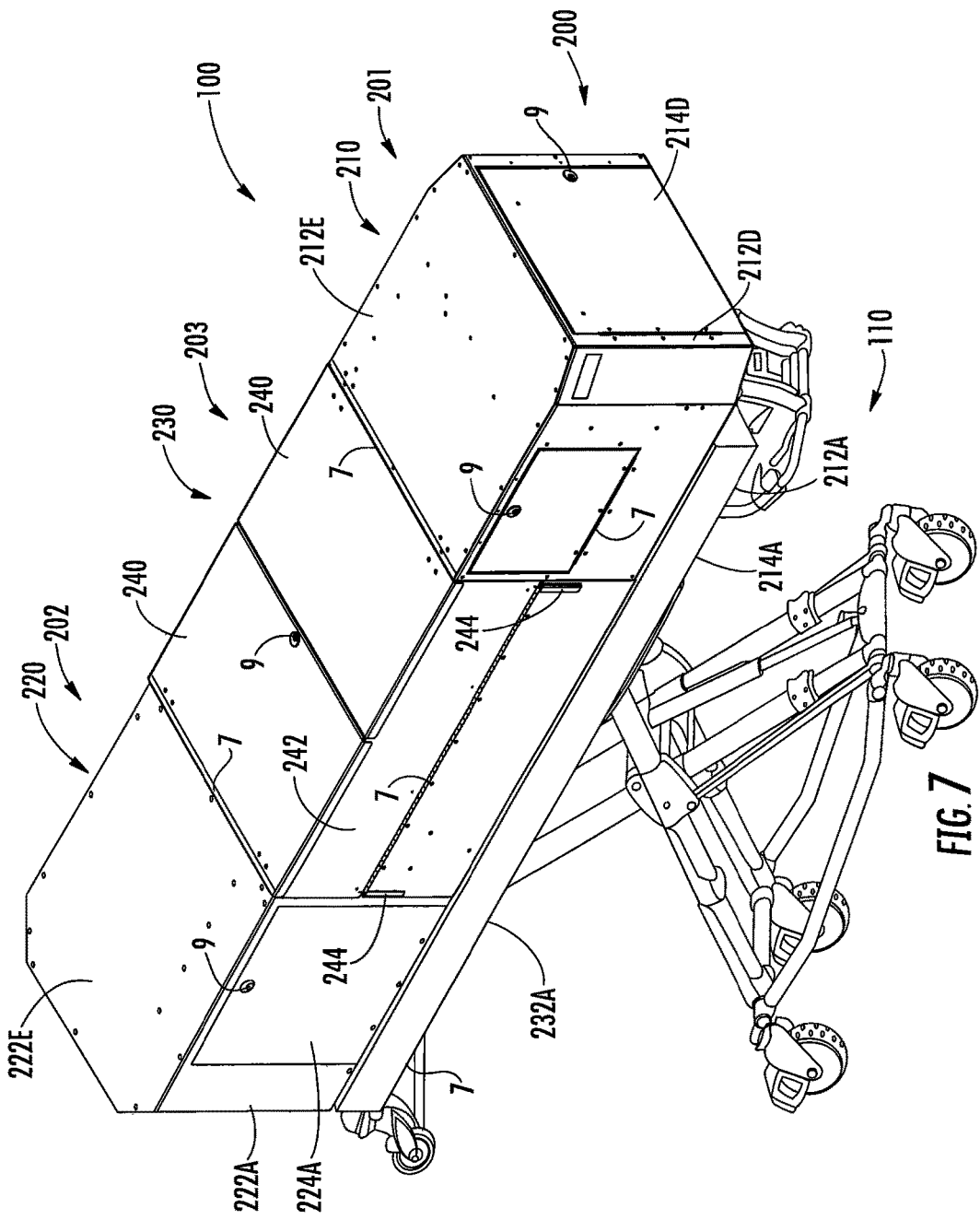
FIG. 7 is a front perspective view of the mobile driver license examination workstation of FIG. 1.
Figure 8:
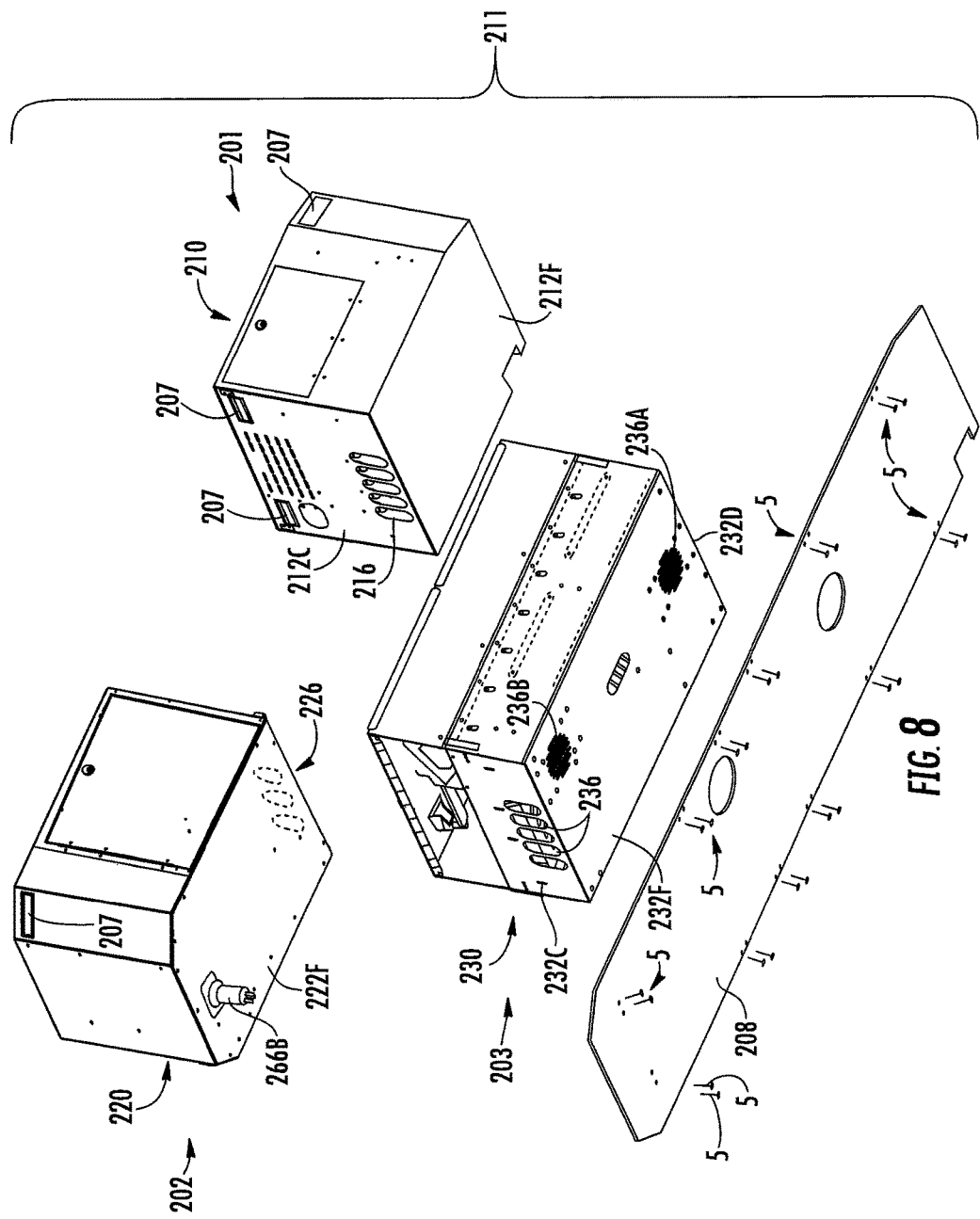
FIG. 8 is an exploded, fragmentary, bottom perspective view of the mobile driver license examination workstation of FIG. 1.

The operator then uses the controller 150 to actuate the actuator 148 to lower the base frame 130 as shown in FIG. 6. After the wheels 134 assume the load of the workstation 100, the cradle arms 40 are lowered (automatically or in response to an operator control input) by the actuator 44 to disengage from the support frame 120 as shown in FIG. 6. The operator then releases the guide wheels 124 from the safety latch mechanism 46.

The mobile workstation 100 is then rolled to a desired location at the worksite. At the chosen location, the wheels 134 are secured using the wheel locks 134A to prevent the workstation 100 from rolling.

The mobile workstation 100 is then transitioned from the closed configuration to its open, operational configuration as shown in FIGS. 9-12.

The doors 214A, 214B, 214C, 224A, 224B are each unlocked and opened. The components in the compartments 210A, 220A, 230B are then accessible and each may be pulled out of its compartment or retained therein until needed. The top panels 240 are removed to expose the work surface 231. The extension supports 244 are pulled out on the front and rear sides of the cabinet 200. The extension panels 242 are folded down onto the supports 244, thereby forming the extended work surface 233. The top door 234 can be unlocked and opened to access the lower compartment 230A and the contents thereof. Ordinarily, the top door 234 will be returned to a locked position in order to secure the contents of the lower compartment 230A. The privacy shield 217 is raised.

The power cord 266 is extended from the reel 266A and plugged into a power supply. Electrical power from this power supply may be distributed through the power block 282 and used to power the components of the workstation 100 throughout its deployment.

Figure 9:
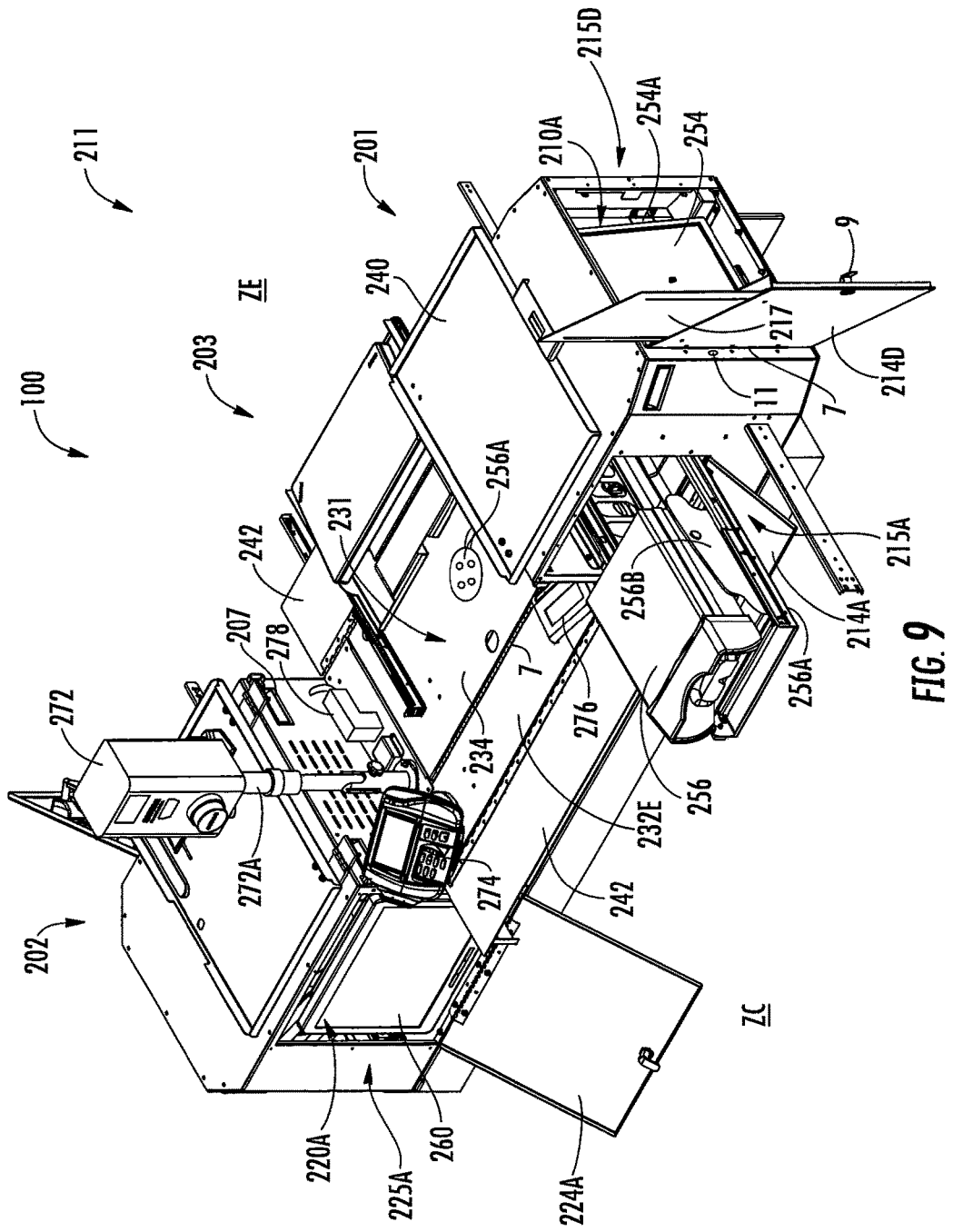
FIG. 9 is a fragmentary, front perspective view of the mobile driver license examination workstation of FIG. 1, wherein the mobile driver license examination workstation is in an operational configuration.
Figure 10:
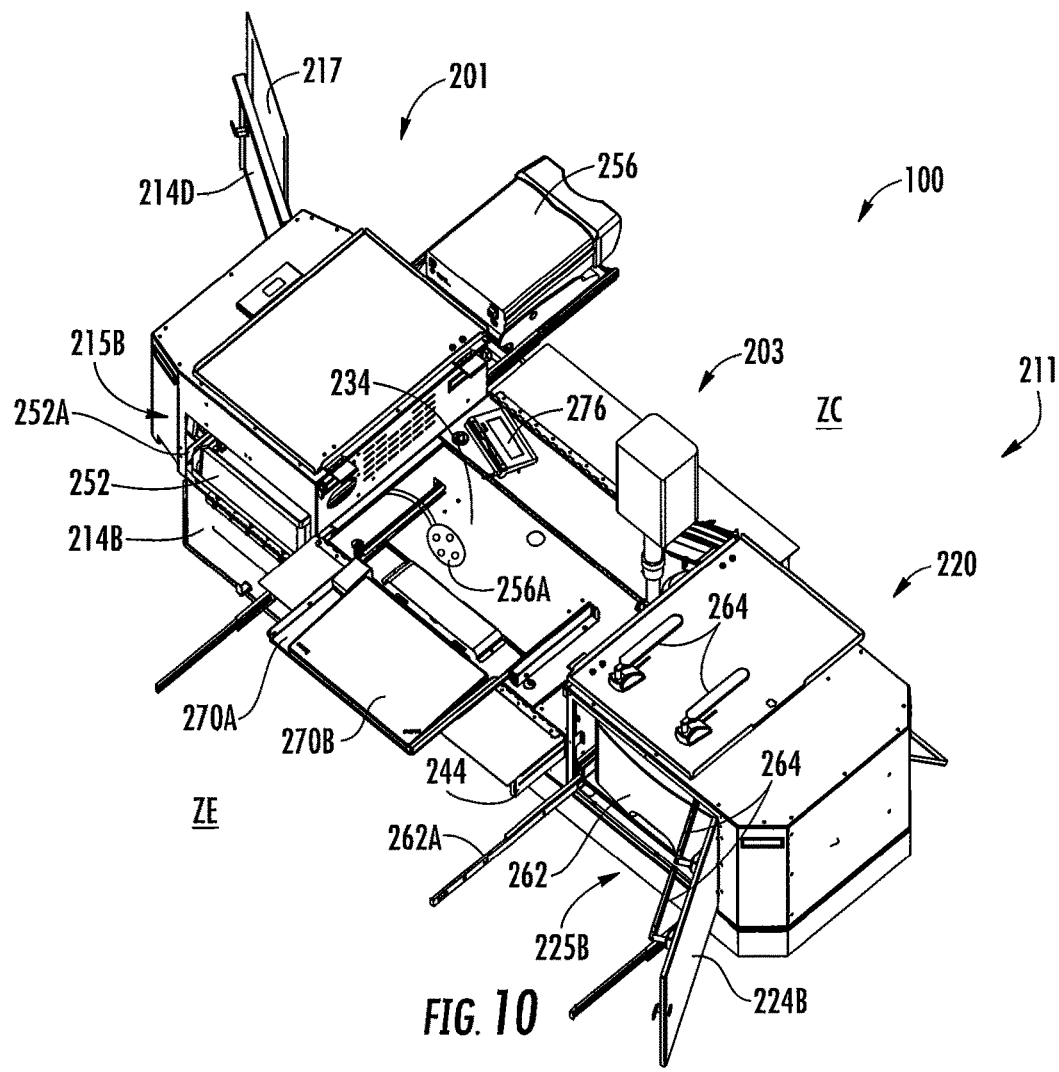
FIG. 10 is a fragmentary, rear perspective view of the mobile driver license examination workstation of FIG. 1, wherein the mobile driver license examination workstation is in the operational configuration.
Figure 11:
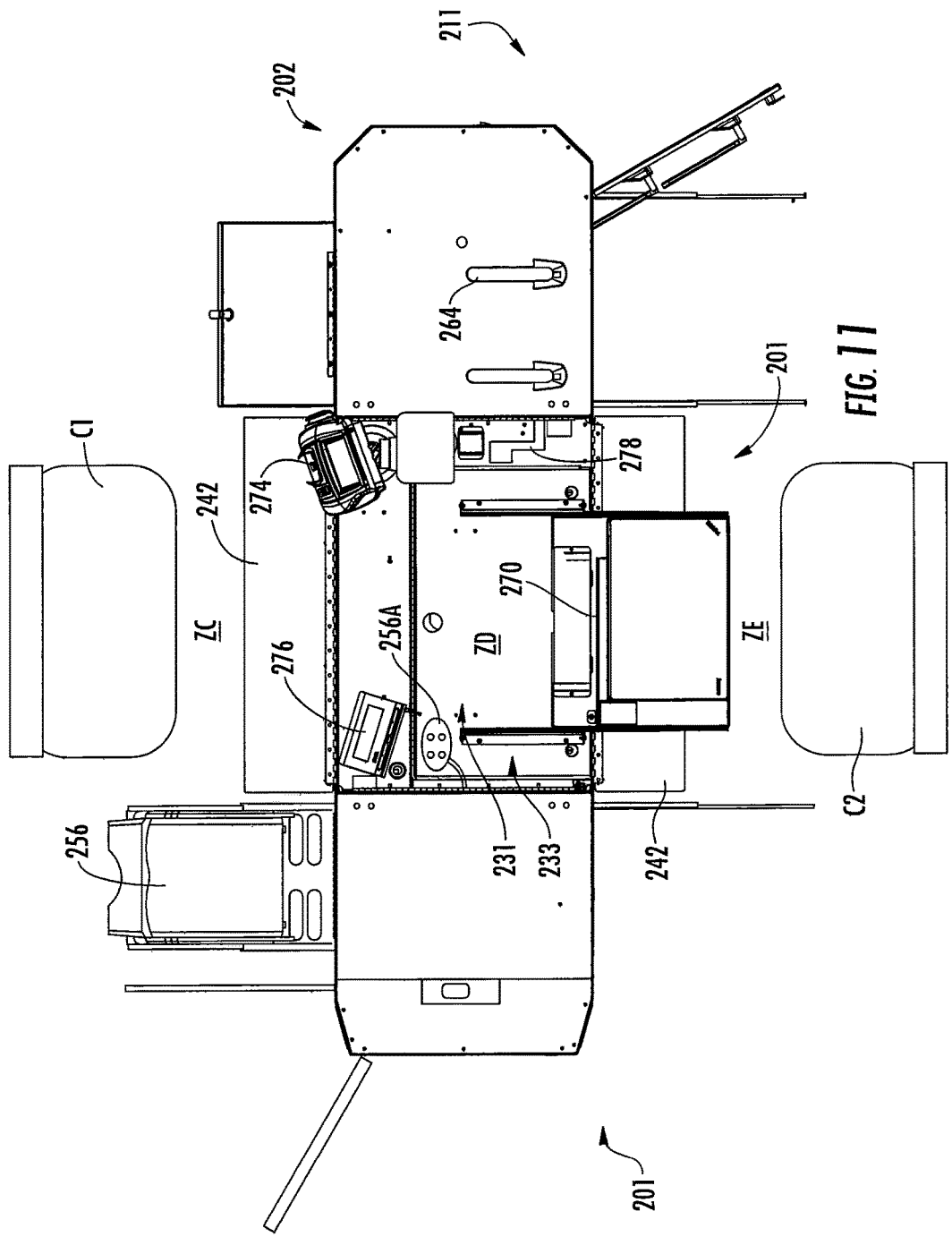
FIG. 11 is a top plan view of the mobile driver license examination workstation of FIG. 1 and two chairs, wherein the mobile driver license examination workstation is in the operational configuration.
Figure 12:
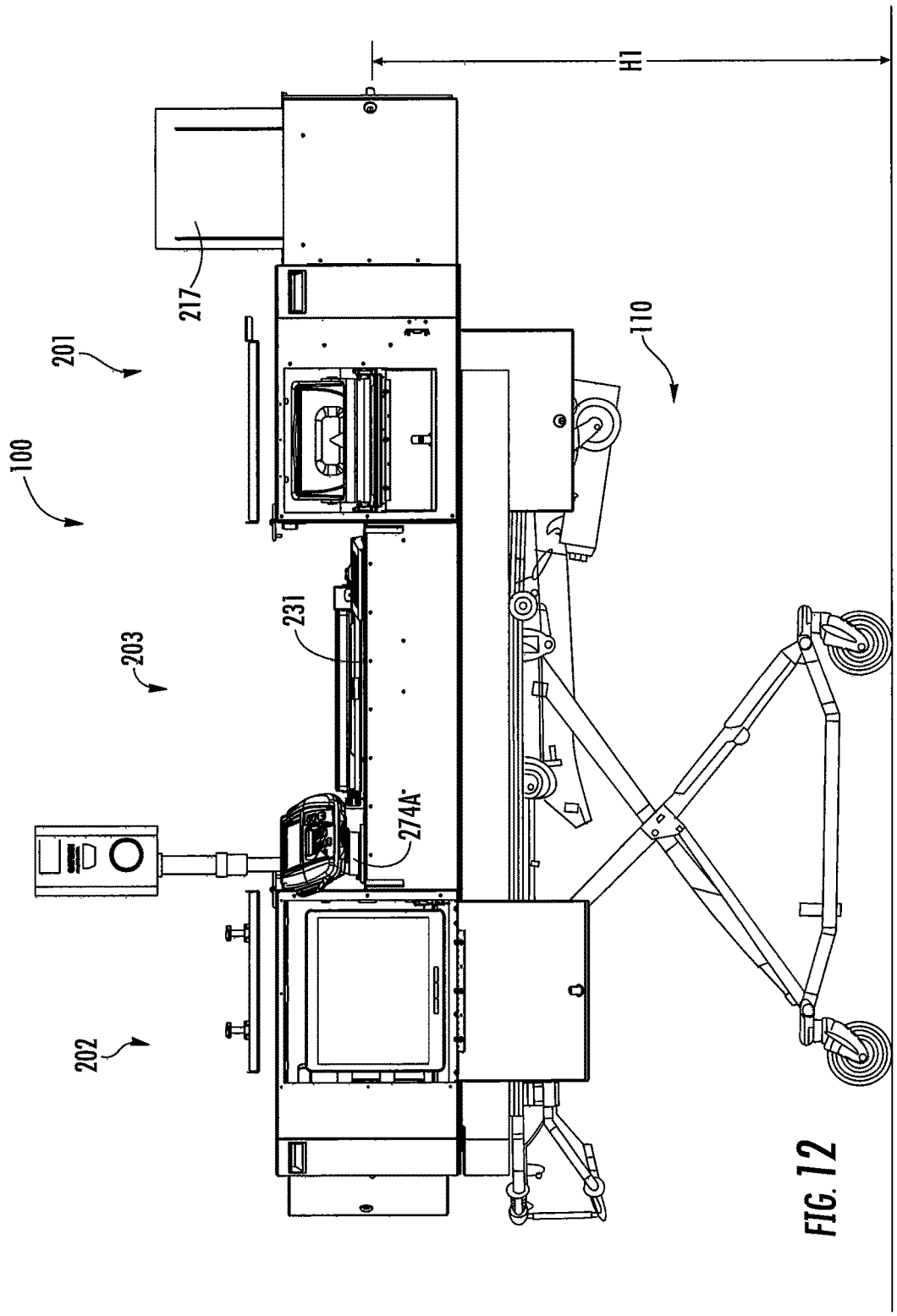
FIG. 12 is a front elevation view of the mobile driver license examination workstation of FIG. 1, wherein the mobile driver license examination workstation is in the operational configuration.
Figure 13:
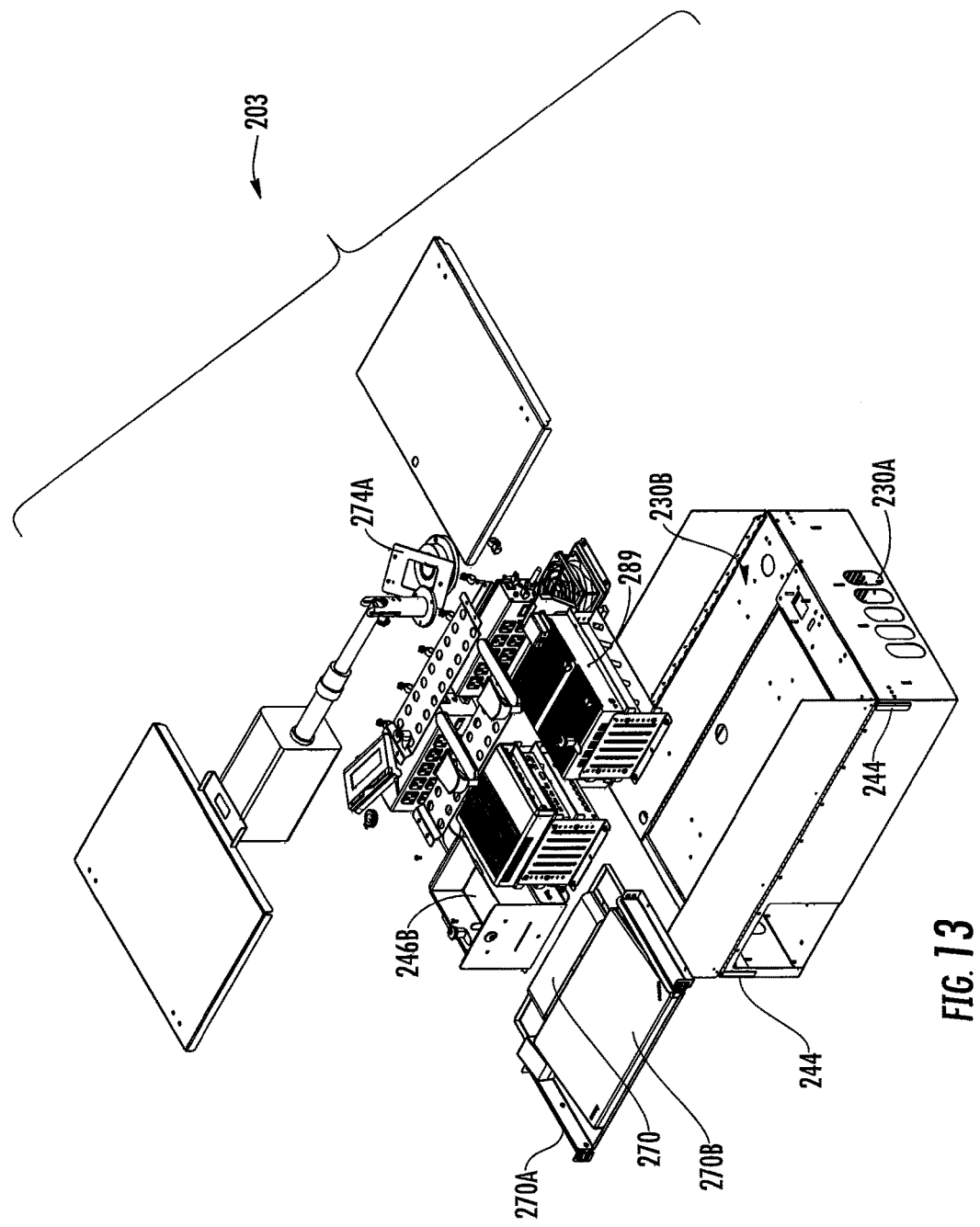
FIG. 13 is an exploded, rear perspective view of a center module forming a part of the mobile driver license examination workstation of FIG. 1.
Figure 14:
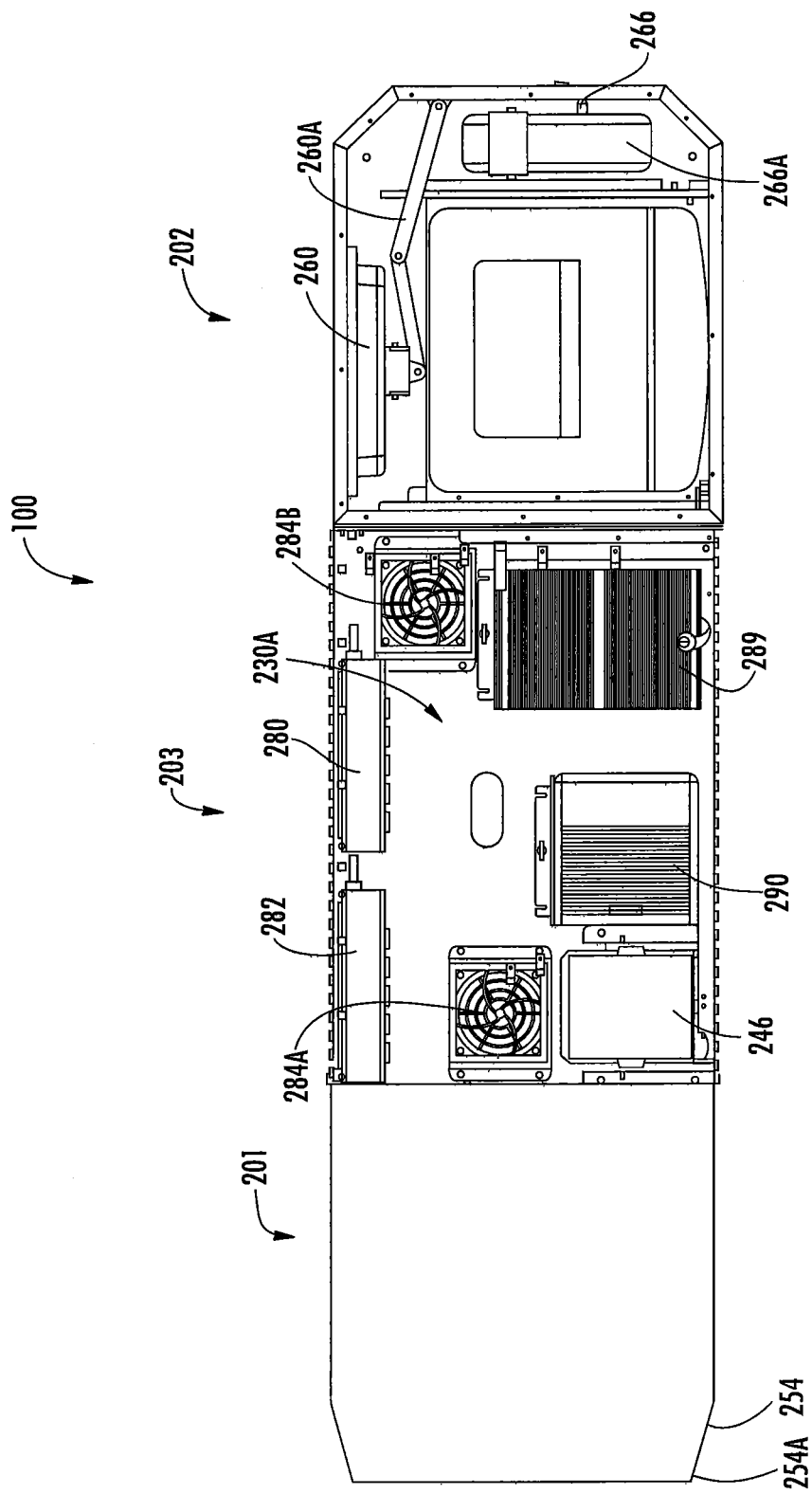
FIG. 14 is a fragmentary, top plan view of the mobile driver license examination workstation of FIG. 1, wherein the mobile driver license examination workstation is in a storage configuration and selected panels and doors of the mobile driver license examination workstation are removed to permit viewing of interior compartments for the purpose of explanation.
Figure 15:
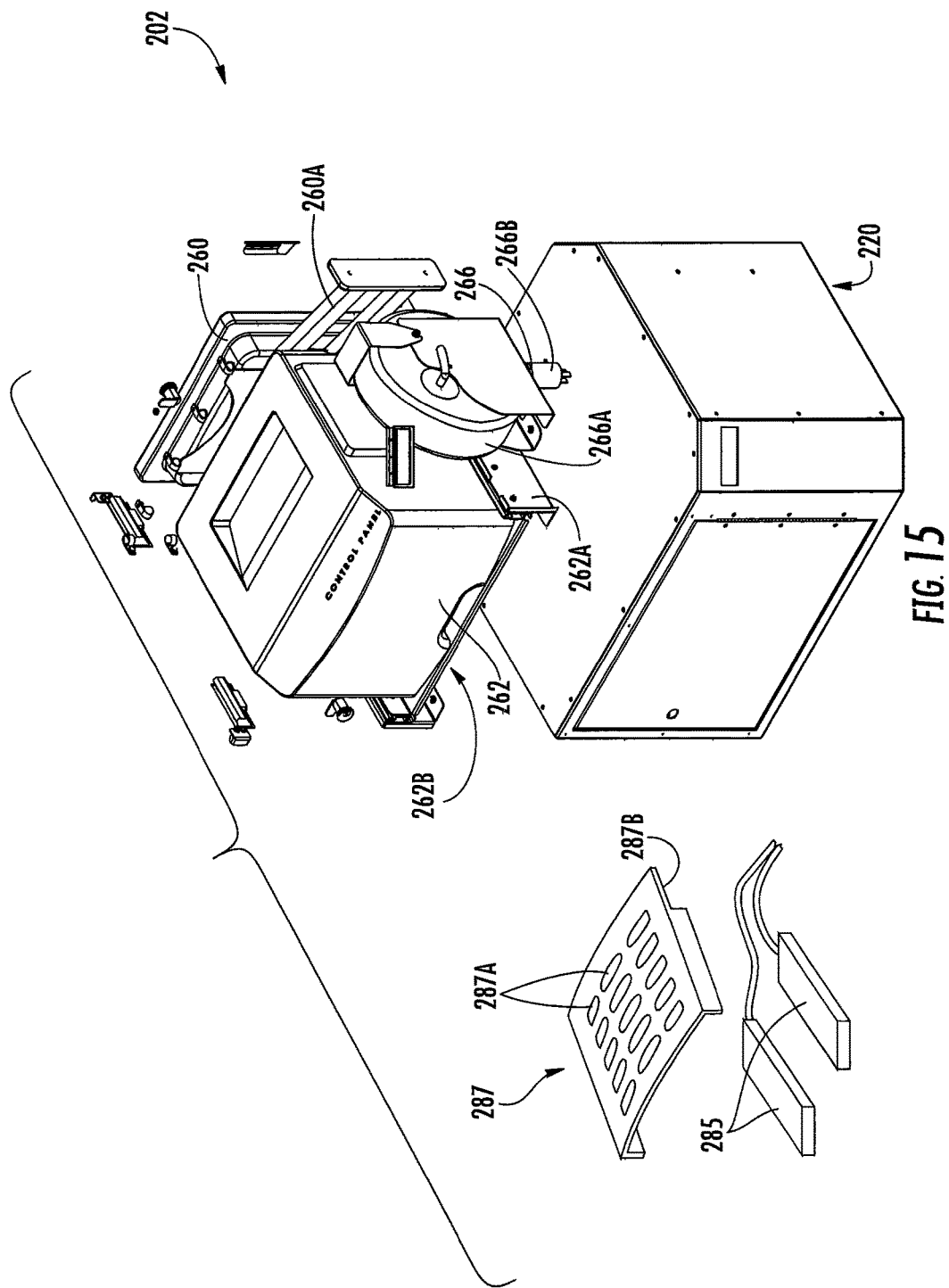
FIG. 15 is an exploded, rear perspective view of an end module forming a part of the mobile driver license examination workstation of FIG. 1.

The lap top computer 270B is installed on the dock 270. The credit card reader 274 is installed on the base 274A. The camera stand 272A is erected with the camera 272 mounted thereon. The signature pad 276 and the bar code reader are positioned for easy access by the customer and the examiner, respectively (e.g., on the work surface 231, as shown in FIG. 9).

Using the controller 150 and the powered lifting mechanism 140, the support frame 120 is raised to a desired height above the ground. In some embodiments, the support frame 120 is raised until the height H1 (FIG. 12) of the work surface 231 above the ground G is at an Americans with Disabilities Act (ADA)-compliant height for a seated examiner. According to some embodiments, the height H1 is in the range of from about 28 to 32 inches.

The workstation 100 defines a customer zone ZC on one side (i.e., the side of the doors 214A, 224A) and an examiner zone ZE on the opposite side (i.e., the side of the doors 212B, 224B). The opened center module 203 forms an integral desk ZD between and for use by both the customer and the examiner. The desk ZD is positioned and configured for comfortable and convenient use by a customer seated in a chair C1 in the zone ZC and an examiner seated in a chair C2 in the zone ZE.

The customer and the examiner can use the several components of the workstation 100 to execute the various actions typically executed in a dedicated state department of motor vehicles facility. These actions may include examination and testing procedures, financial transaction procedures, background check procedures, certification issuance procedures, and voter registration procedures. A motor vehicle operator license examination may include a vision test, a knowledge test, collection and confirmation of biographical and other customer information, and payment of a requisite fee. The several stations may be used as described below to accomplish these tasks.

The examiner may be seated in a chair C2 in the examiner zone ZE facing the work surface 231. The examiner may slidably adjust the position of the platform 270A to position the laptop computer 270B as desired (e.g., adjacent or over the proximate extension panel 242). From this position, the examiner will also have convenient access to the camera 272, the scanner 252, the barcode reader 278, the vision tester controller 256C, the printer 262, and the drawer 246.

The customer may be seated in a chair C1 in the customer zone ZC facing the work surface 231. From this position, the customer will have convenient access to the vision tester 256, the credit card reader 274, and the signature acquisition pad 276. The customer also can easily view the display monitor 260. The customer or another customer may also sit adjacent the end of the first module 210 in order to view and enter inputs on the touchscreen monitor 254.

The examiner can acquire biographical and other data regarding the customer by scanning a barcode on the customer's existing identification document (e.g., a driver's license) using the barcode reader 278. The information acquired from the barcode may be displayed on the laptop 270B and also on the display monitor 260. The examiner may instruct the customer to review this and/or other information on the display 260 to confirm and update the data.

The examiner may also communicate with a remote server via the antennae 264 to acquire additional information about the customer and/or to update a remote database. For example, the examiner may conduct a background check on the customer and access the customer's driving record, criminal record, court records or the like from the remote server.

The customer may undertake a vision test using the vision tester unit 256, which is controlled by the examiner using the controller 256C. The turntable 256A can be used to adjust the position of the vision tester unit 256 to fit the customer. The turntable 256A may also include height and tilt adjustability.

The customer may undertake a knowledge test using the touchscreen display 254. The test-taking customer may likewise be seated in a chair. A customer may be positioned at the end of the cabinet 110 to use the touchscreen display 254 to take a test while another customer is seated in the customer zone ZC. The primary shield 217 can provide the test-taker with privacy and can reduce distraction.

The examiner may use the scanner 252 to scan documentation provided by the customer, forms executed by the customer, or other documents for which stored images are required or desired.

The printer 262 can be used to print forms or transaction receipts. In some embodiments, the printer 262 is used to print a voter registration form populated with data supplied by the customer or the scanned barcode. The voter registration form may be executed by the customer and scanned or physically stored for further processing.

The workstation 100 is equipped to process payment of different types. Payment by money bills or check can be inserted into the drawer subchamber 246C through the slot 246A. Credit card payment (including debit cards) may be executed using the credit card reader 274 and the signature acquisition pad 276. The credit card payment data is locally processed and communicated wirelessly via the antennae 264 to a remote credit card processing server or vendor. Notably, the top door 234 and the drawer 246 can remain locked and closed throughout operation so that the system remains PCI compliant.

In case of a loss of power from the power supply, the onboard backup battery 280 may serve to provide power to some components of the workstation. In particular, the battery 280 may supply emergency backup power to the credit card reader 274, signature pad 276, credit card processing module 288 and cellular radio to enable the examiner to complete a credit card transaction.

During use, the fans 284A, 284B circulate air through the compartment 230A to cool the components therein. In this manner, the lives of the electronic components may be extended. The fans 284A, 284B may be configured to run continuously or may be controlled (e.g., by a manual switch, timer or thermostat).

When not in use, the workstation 100 can be secured against theft and tampering by returning the components to their respective compartments and closing and locking the doors and cover panels so that the workstation 100 is returned to its closed configuration.

The workstation 100 can be installed at the work site and used as described above for as long as desired. When it is desired to relocate the workstation 100 to another site, the workstation 100 is returned to its closed configuration as described above and shown in FIGS. 1 and 7. The workstation 100 is then rolled to the vehicle rear opening 28 and raised to a height adjacent the trolley 34. With the cradle arms 40 lowered, the workstation 100 is rolled toward the trolley 34 until the guide wheels 124 are received and locked into the safety latch mechanism 46. The cradle arms 40 are then raised by the actuator (automatically or in response to operator input) to engage the underside of the support frame 120 and lift or hoist the workstation 100. With the weight of the workstation 100 supported by the cradle arms 40, the operator raises the base frame 130 using the lifting mechanism 140. Once the base is raised to clear the vehicle floor 26, the operator pushes the trolley 34 along the guide track 32 in direction C to the rear of the cargo volume 24. The deployment system 30 may then automatically lock the trolley 134 in position along the guide track 32 and lower the cradle arms 40 so that the wheels 134 rest on the vehicle floor 26. The workstation 100 can now be transported, deployed and used in the same manner as described above at a further work site.

Mobile workstations, systems and methods as disclosed herein can provide improved durability, flexibility, adaptability, versatility, cost-effectiveness and convenience in providing equipment for motor vehicle operator's license examination at a remote site. The mobile workstation can serve as an operationally complete remote office. Furthermore, the mobile workstation system 10 can enable the mobile workstation 100 to be deployed easily and expeditiously with reduced risk and injury. Because the deployment system 30 assists in loading and unloading the workstation from the vehicle, the operator is not required to lift and engage in strenuous exertion.

The modular configuration of the mobile workstation can facilitate repair or upgrade of the workstation 100. In particular, each of the subcabinets 210, 220, 230 and the modules 201, 202, 203 can be individually removed (by removal of the associated fasteners 5) from the carrier 110 and re-mounted on the carrier 110 (if repaired or upgraded) or replaced with a new subcabinet or module. The integral handles 207 can be used to handle, lift and carry the subcabinets 210, 220, 230. The cabling and interconnections within the workstation 100 also facilitate convenient repair and replacement of the components. Thus, the workstation 100 can be easily serviced in the field.

The workstation 100 may be provided with additional connectivity including a USB connector, an Ethernet connector and/or a telephone (e.g., RJ-45) connector for connecting components of the workstation to external communications equipment.

In order to provide weather resistance, the doors and/or other panels may be provided with gaskets (e.g., elastomeric) along their edges. A supplemental cover may be provided to cover the cabinet 200 when the workstation 100 is not in use.

A skirt may be mounted on the workstation 100 to circumferentially cover the carrier 110. The skirt may be formed of a flexible, compliant material such as vinyl and may bear indicia and/or other graphics. Indicia and/or other graphics may also be provided on the cabinet 200.

The workstation 100 may be provided with integral lights. These lights may be particularly useful to light a path of travel between the vehicle and the set up location.

Although only one power cable 266 is shown, the workstation 100 may be provided with multiple power cables.

The drawer slides as disclosed hereinabove may be locking drawer slides.

The vehicle 20 may be equipped with two side-by-side deployment systems 30 and a mobile workstation 100 mounted on each.

The system 10 may be further equipped with an auxiliary generator such as a mobile gasoline-powered generator. The generator may be carried or towed by the vehicle 20 and used to provide electrical power to the mobile workstation 100 at the work site.

While the mobile workstation system 10 and the mobile workstation 100 are described hereinabove configured and used for use as a remote motor vehicle operator examination workstation, in other embodiments aspects of the system 10 and workstation 100 may be used for other applications. For example, the workstation 100 may be reconfigured for other uses and deployed using the deployment system 30. Such other uses may include, for example, administering and processing claims (e.g., insurance claims or claims for public relief benefits) onsite in the event of a disaster.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A mobile workstation system comprising:
   a transport vehicle including a cargo volume;
   a mobile workstation including:
      a wheeled carrier;
      a cabinet supported by the carrier, the cabinet defining at least one enclosed compartment and having selectively openable closures to provide access to the at least one compartment; and
      a plurality of operational components disposed in the at least one compartment;
      wherein the mobile workstation is positionable in each of:
         a storage configuration wherein the operational components are contained in the at least one compartment with the closures in a closed position; and
         an operational configuration wherein the closures are open to provide access to the operational components and the cabinet forms a desk including a work surface; and
   a deployment system mounted in the transport vehicle and including a powered engagement mechanism operable to load and unload the mobile workstation into and from the cargo volume of the vehicle.

2. The mobile workstation system of claim 1 wherein:
   the mobile workstation is a motor vehicle operator license examination mobile workstation; and
   the operational components include apparatus usable by an examiner to administer motor vehicle operator license examinations.

3. The mobile workstation system of claim 2 wherein:
   the workstation, when in the operational configuration, defines a customer zone and an examiner zone on opposed sides of the workstation and the work surface;
   the apparatus usable by an examiner to administer motor vehicle operator license examinations are accessible to the examiner sitting in the examiner zone; and
   some of the operational components are apparatus usable by a customer taking a motor vehicle operator license examination and are accessible to the customer sitting in the customer zone.

4. The mobile workstation system of claim 2 wherein the apparatus usable and accessible by a customer sitting in the customer zone include a vision testing unit.

5. The mobile workstation system of claim 2 wherein the apparatus usable and accessible by a customer sitting in the customer zone include an electronic payment terminal.

6. The mobile workstation system of claim 2 wherein the operational components include a camera positioned to photograph a customer sitting in the customer zone.

7. The mobile workstation system of claim 1 wherein:
   the deployment system includes a guide track affixed to the transport vehicle in the cargo volume;
   the deployment system further includes a trolley mounted on the guide track to travel axially along the guide track; and
   the powered engagement mechanism includes a cradle arm configured to engage the mobile workstation and a force actuator to drive the cradle arm.

8. The mobile workstation system of claim 1 wherein the carrier includes a powered height adjustment mechanism.

9. The mobile workstation system of claim 1 wherein:
   the cabinet includes a plurality of subcabinets; and each of the subcabinets defines a respective compartment containing one or more of the operational components and has a selectively openable closure.

10. The mobile workstation system of claim 9 wherein each of the subcabinets and the operational component(s) contained therein form a module that is secured to the carrier and removable from the carrier independently of the other subcabinets.

11. The mobile workstation system of claim 1 wherein the mobile workstation includes:
   electronic components disposed in a compartment of the cabinet; and
   at least one cooling fan operative to generate a flow of ambient air through the compartment to cool the electronic components.

12. The mobile workstation system of claim 1 wherein the mobile workstation includes a power supply connection to provide electrical power to one or more of the operational components.

13. The mobile workstation system of claim 1 wherein at least one of the closures is provided with a lock.

14. The mobile workstation system of claim 1 wherein the carrier includes a powered height adjustment mechanism.

15. A method for providing a workstation, the method comprising:
   providing a mobile workstation system comprising:
      a transport vehicle including a cargo volume;
      a mobile workstation including:
         a wheeled carrier;
         a cabinet supported by the carrier, the cabinet defining at least one enclosed compartment and having selectively openable closures to provide access to the at least one compartment; and
         a plurality of operational components disposed in the at least one compartment;
         wherein the mobile workstation is positionable in each of:
            a storage configuration wherein the operational components are contained in the at least one compartment with the closures in a closed position; and
            an operational configuration wherein the closures are open to provide access to the operational components and the cabinet forms a desk including a work surface; and
      a deployment system mounted in the transport vehicle and including a powered engagement mechanism operable to load and unload the mobile workstation into and from the cargo volume of the vehicle;
   using the transport vehicle, transporting the mobile workstation in the cargo volume with the mobile workstation in the storage configuration; thereafter unloading the mobile workstation from the vehicle using the deployment system; and thereafter converting the mobile workstation to the operational configuration.

16. The method of claim 15 wherein:
   the deployment system includes a guide track affixed to the transport vehicle in the cargo volume;
   the deployment system further includes a trolley mounted on the guide track to travel axially along the guide track;
   the powered engagement mechanism includes a cradle arm configured to engage the mobile workstation and a force actuator to drive the cradle arm; and
   the method includes, with the mobile workstation mounted on the trolley and supported by the cradle arm, sliding the trolley on the guide track toward an opening of the transport vehicle until the mobile workstation extends outwardly beyond the opening.

17. The method of claim 16 including, after the step of sliding the trolley on the guide track toward an opening of the transport vehicle until the mobile workstation extends outwardly beyond the opening:
   with the mobile workstation supported by the cradle arm, lowering a frame assembly of the wheeled carrier to support the mobile workstation on the ground; thereafter
   lowering the cradle arm; and thereafter
   rolling the mobile workstation away from the transport vehicle.

18. A mobile workstation comprising:
   a wheeled carrier;
   a cabinet supported by the carrier, the cabinet defining at least one enclosed compartment and having selectively openable closures to provide access to the at least one compartment; and
   a plurality of operational components disposed in the at least one compartment;
   wherein the mobile workstation is positionable in each of:
      a storage configuration wherein the operational components are contained in the at least one compartment with the closures in a closed position; and
      an operational configuration wherein the closures are open to provide access to the operational components and the cabinet forms a desk including a work surface; and
   wherein:
      the mobile workstation is a motor vehicle operator license examination mobile workstation; and
      the operational components include apparatus usable by an examiner to administer motor vehicle operator license examinations.

19. The mobile workstation of claim 18 wherein:
   the workstation, when in the operational configuration, defines a customer zone and an examiner zone on opposed sides of the works station and the work surface;
   the apparatus usable by an examiner to administer motor vehicle operator license examinations are accessible to the examiner sitting in the examiner zone;
   some of the operational components are apparatus usable by a customer taking a motor vehicle operator license examination and are accessible to the customer sitting in the customer zone;
   the apparatus usable and accessible by a customer sitting in the customer zone include a vision testing unit;
   the apparatus usable and accessible by a customer sitting in the customer zone include an electronic payment terminal; and
   the operational components include a camera positioned to photograph a customer sitting in the customer zone.

20. The mobile workstation of claim 18 wherein:
   the cabinet includes a plurality of subcabinets;
   each of the subcabinets defines a respective compartment containing one or more of the operational components and has a selectively openable closure; and
   each of the subcabinets and the operational component(s) contained therein form a module that is secured to the carrier and removable from the carrier independently of the other subcabinets.

* * * * *

UNITED STATES PATENT AND TRADEMARK OFFICE
CERTIFICATE OF CORRECTION

PATENT NO. : 10,085,632 B1
APPLICATION NO. : 15/288464
DATED : October 2, 2018
INVENTOR(S) : Dishong et al.

Page 1 of 1

It is certified that error appears in the above-identified patent and that said Letters Patent is hereby corrected as shown below:

In the Specification

Column 8, Line 21: Please correct "2140" to read -- 214D --

Signed and Sealed this
Eighth Day of January, 2019

Andrei Iancu
*Director of the United States Patent and Trademark Office*